United States Patent [19]

La Thangue et al.

[11] Patent Number: 5,859,199
[45] Date of Patent: Jan. 12, 1999

[54] TRANSCRIPTION FACTOR DP-3 AND ISOFORMS THEREOF

[75] Inventors: Nicholas B. La Thangue; Susana de la Luna, both of Glasgow, United Kingdom

[73] Assignee: Prolifix Limited, London, United Kingdom

[21] Appl. No.: 723,415

[22] Filed: Sep. 30, 1996

[30] Foreign Application Priority Data

May 15, 1996 [GB] United Kingdom .................... 9610195

[51] Int. Cl.$^6$ ...................................................... C07K 14/47
[52] U.S. Cl. ........................... 530/350; 530/300; 530/324
[58] Field of Search ....................................... 530/300, 350,
530/324, 325, 326, 327, 328, 329, 330

[56] References Cited

FOREIGN PATENT DOCUMENTS

| | | |
|---|---|---|
| WO 93/15227 | 8/1993 | WIPO . |
| WO 93/23539 | 11/1993 | WIPO . |
| WO 94/10307 | 5/1994 | WIPO . |
| WO 94/12521 | 6/1994 | WIPO . |
| WO 96/01425 | 1/1996 | WIPO . |
| WO 97/02354 | 1/1997 | WIPO . |
| WO 97/43647 | 11/1997 | WIPO . |

OTHER PUBLICATIONS

Magae et al, Journal of Cell Science, vol. 109, pp. 1717–1726, 1996.
Altmann et al, TIBS 18 Nov. 1993 pp. 429–432.
Bandara et al, The EMBO Journal vol. 12 No. 11 pp. 4317–4324 1993.
Bandara, The EMBO Journal vol. 13 No. 13, pp. 3104–3114, 1994.
Beijersbergen et al, Genes & Development 8:2680–2690 pp. 2680–2690.
Boulikas, J. Cellular Biochemistry 55:32–58 1994.
Boulikas, Critical Reviews in Eukaryotic Gene Expression, 3(3):193–227 (1993).
Buck et al, Oncogene (1995) 11, 31–38.
Chang et al, J. of Virology 1995 vol. 69 No. 2 pp. 801–808.
Cobrinik et al, Genes & Development 7:2392–2404 1993.
Descombes et al, Cell, vol. 67 569–579 Nov. 1991.
Dingwall et al, TIBS 16 Dec. 1991, pp. 478–481.
Dynlacht et al, Genes & Development 1994 pp. 1772–1786.
Fields et al, Letters to Nature vol. 340 pp. 245–246 1989.
Flemington et al, Proc. Natl. Acad. Sci. USA vol. 90 pp. 6914–6918 1993.
Geballe et al, TIBS 19 1994 pp. 159–164.
Ginsberg et al, Genes & Development 8:2665–2679 1994.
Girling et al, Nature vol. 362 1993 pp. 83–87.
Girling et al, Molecular Biology of the Cell vol. 5, 1081–1092, 1994 pp. 1081–1092.
Helin et al, Cell vol. 70, 337–350 1992.
Helin et al, Genes & Development 7:1850–1861 1993.
Molecular and Cellular Biology vol. 13, No. 10, 1993 pp. 6501–6508.
Hiebert et al., Gene & Development 6:177–185 1992.
Hill et al, J. Biological Chemistry 1993 vol. 268, No. 1, Jan. 5 issue pp. 726–731.
Hill et al, Cell 1995 pp. 199–211 (vol. 80).
Hoyle et al, Molecular and Cellular Biology vol. 13, No. 12 1993, pp. 7802–7812.
Kaelin et al, Cell, 70 351–364, 1992.
Kozak, Nucleic Acids Research vol. 15, No. 10 1987 pp. 8125–8148.
Krek et al, Cell 78 161–172 1994.
Krek et al, Science vol. 262 1993 pp. 1557–1560.
La Thangue et al, Nucleic Acids Research, vol. 18 No. 10 pp. 2929–2938.
La Thangue, TIBS 19 1994 pp. 108–114.
Lam et al, Current Opinion in Cell Biology 1994, 6:859–866.
Ormondroyd et al, Oncogene 1995, 11, 1437–1446.
Lees et al, Molecular and Cellular biology, 1993, vol. 13(12):7813–7825.
Lees et al, Genes & Development 6:1874–1885.
Li et al, Genes & Devlopment 1993 vol. 5: pp. 2366–2377.
Ngo et al, The Protein Folding Problem and Tertiary Structure Prediction, 1994, Mertz et al. (eds.), Birkhauser, Boston, MA, pp. 433 and 492–495.

*Primary Examiner*—Terry McKelvey
*Attorney, Agent, or Firm*—Nixon & Vanderhye, P.C.

[57] ABSTRACT

The invention provides polypeptides of transcription factor DP-3 which exists in four isoforms produced by alternative splicing of mRNA, nucleic acid encoding the polypeptides and the use of such nucleic acid and polypeptides in assays. Two isoforms of DP-3 contain a region, designated the E region, which is a nuclear localization signal and is involved in a further level of regulation of DP-3 and its ability to bind to E2F-1 and regulate the cell cycle.

2 Claims, 2 Drawing Sheets

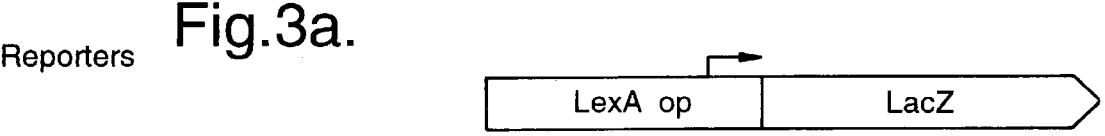
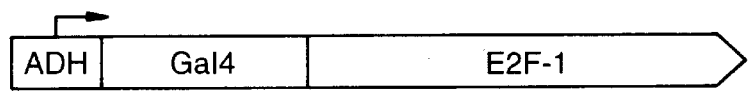
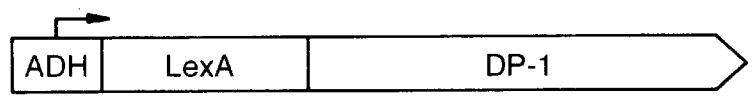
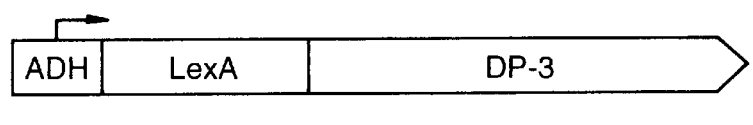
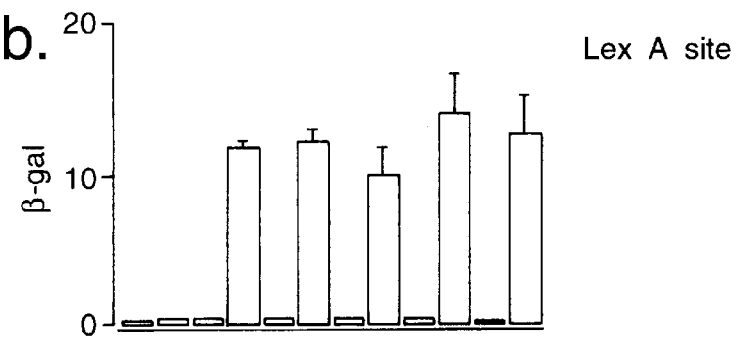
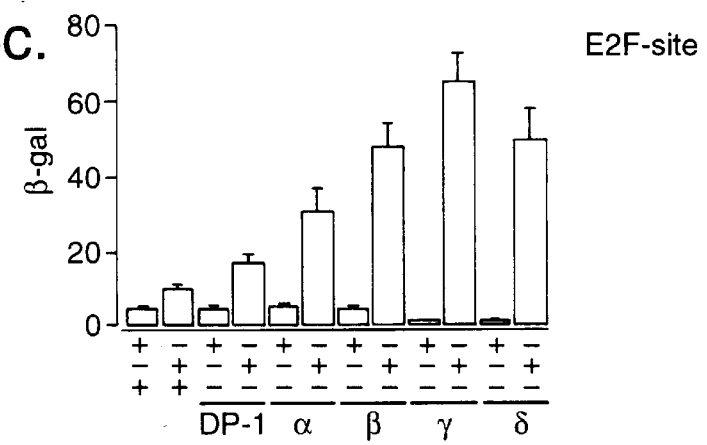

TRANSCRIPTION FACTOR DP-3 AND ISOFORMS THEREOF

The present invention relates to a new member of the cell cycle transcription factor DRTF1/E2F family, DP-3, with distinct protein products produced by alternative splicing. The invention further relates to the use of a nuclear localization signal in DP-3 as a target for novel assays.

BACKGROUND TO THE INVENTION

A wealth of cell cycle research supports the idea that the cellular transcription factor DRTF1/E2F plays a pivotal role in coordinating early cell cycle events by integrating transcription with cell cycle progression (Nevins, 1992; La Thangue, 1994). For example, the negative effects on cellular proliferation exerted by the retinoblastoma tumour suppressor gene product (pRb) appear to be mediated in part through the ability of pRb to regulate the transcriptional activity of DRTF1/E2F (Heibert et al., 1992; Zamanian and La Thangue, 1992). Since many target genes encode proteins which contribute to cell cycle progression, pRb may influence proliferation through a regulation of DRTF1/E2F. The importance of this pathway in cell cycle control is underscored by the fact that natural mutations in Rb, which frequently occur in human tumour cells, encode proteins which fail to bind to DRTF1/E2F and that the oncogene products of certain tumour viruses, such as adenovirus Ela, human papilloma virus E7 and SV40 large T antigen bind pRb, an interaction which correlates with a potential to mediate cellular transformation (Nevins, 1992; La Thangue, 1994).

Other members of the pRb family (known generically as 'pocket proteins') interact with DRTF1/E2F and regulate its transcriptional activity. Two other members of the family, plO7 and p130, associate with DRTF1/E2F in temporally distinct fashions during cell cycle progression, p130 predominantly during G0 and p107 in late G1 and into S phase (Shirodkar et al., 1992; Cobrinik et al., 1993). Like pRb, the physical association of p107 leads to transcriptional inactivation (Schwarz et al., 1993; Zamanian and La Thangue, 1993), and p107 can negatively regulate cell cycle progression (Zhu et al., 1993) but in contrast to Rb is not known to be mutated in tumour cells.

Several other molecules involved in regulating the cell cycle interact with DRTF1/E2F. Either cyclin A or E, together with the catalytic kinase subunit cdk2, can stably interact in a fashion which is dependent upon the presence of p107 or p130; again these events are under temporal control during the cell cycle (Lees et al., 1992; Cobrinik et al., 1993; Li et al., 1993). The physiological role of the cyclin A/cdk2 and cyclin E/cdk2 kinase in this context is unknown. In contrast, there is persuasive evidence that cyclins A and E influence the growth regulating capacity of pRb (Hinds et al., 1992). An alternative type of interaction can occur between a cyclin A-dependent kinase and DRTF1/E2F (Dynlacht et al., 1994; Krek et al., 1994). The biochemical consequence of this interaction is reduced DNA binding activity which is believed to be involved with the physiological control of transcription at later times during the cell cycle.

Progress has been made in understanding the molecular composition of DRTF1/E2F. Specifically, generic DRTF1/E2F DNA binding activity arises when members of two distinct families of proteins interact as DP/E2F heterodimers (Lam and La Thangue, 1994), the prototype molecules of each family being E2F-1 (Helin et al., 1992; Shan et al., 1992; Kaelin et al., 1992) and DP-1 (Girling et al., 1993). Heterodimerization between DP and E2F proteins (Bandara et al., 1993; Helin et al., 1993; Krek et al., 1993; Girling et al., 1994) allows a variety of combinatorial interactions to generate an array heterodimers.

Information on the properties of E2F family members suggests that they perform a physiological role in dictating the nature of the pocket protein which physically interacts with the heterodimer. From the E2F family members characterised, it is believed that E2F-1, -2 and -3 interact with pRb (Ivey-Hoyle et al., 1993; Lees et al., 1993), E2F-4 with p107 (Beijersbergen et al., 1994; Ginsberg et al., 1994) and E2F-5 with p130 (Buck et al., 1995). An extreme C-terminal region in these E2F proteins required for the physical association of pocket proteins is interdigitated with a potent trans activation domain (Helin et al., 1993; Flemington et al., 1993). It is likely therefore that the temporally regulated association of pocket proteins with DRTF1/E2F during cell cycle progression reflects its dynamically changing composition.

In many types of cells DP-1 is a frequent component of DRTF1/E2F, for example in 3T3 cells where it is present in DNA binding complexes which occur throughout the cell cycle (Bandara et al., 1994). Another member of the DP family, DP-2, is expressed in a tissue-restricted fashion (Girling et al., 1994). However, apart from this distinction the biochemical and functional properties of DP-1 and DP-2 are similar (Girling et al., 1994).

Recently, two publications have documented the existence of a further member of the DP family of proteins (Wu et al., 1995; Zhang and Chellappan, 1995). The cDNA sequence presented in Wu et al. (1995) is derived from the human DP-3 locus. Zhang and Chellappan (1995) report an identical sequence apart from the addition of a single glutamine at position 97.

DESCRIPTION OF THE DRAWINGS

FIGS. 3a–3c shows DP-3 proteins interact with E2F-1 and activate E2F site-dependent transcription in yeast cells:

Figure 1:
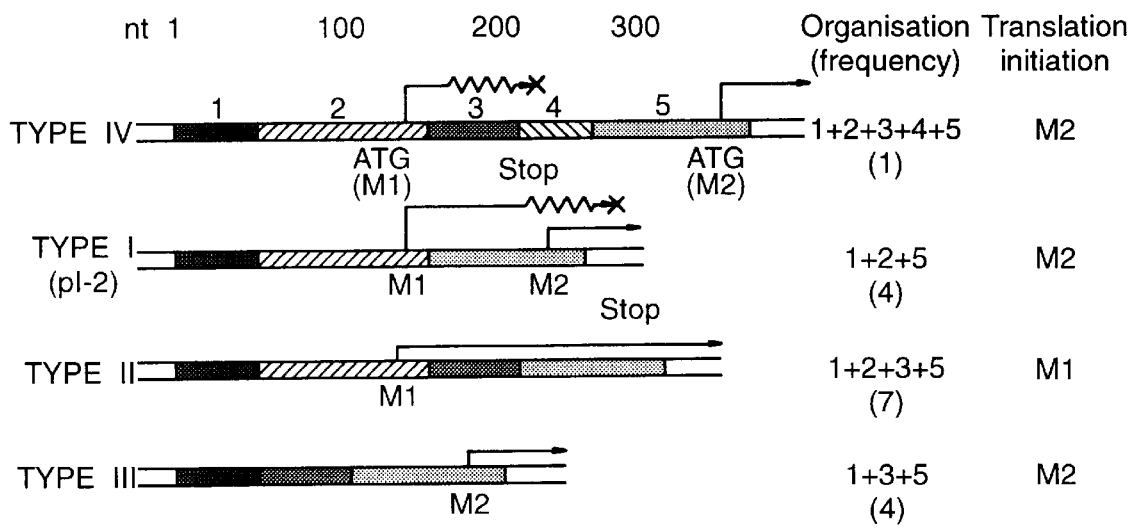
FIG. 1 shows the types of RNA organization in cDNA library clones and cloned PCR products generated by RT PCR using P1 and P2 or P3 with mouse brain or kidney RNA as template. RNA segments were defined by sequence analysis and are numbered 1 to 5 with nucleotide positions relative to the position of the 5' end of the pl-2 cDNA clone (see below), which is 234 nucleotides upstream of M1 indicated above. Potential translation initiation from M1 or M2 is indicated by arrows, and broken when Ml initiation is interrupted by a stop codon (*) in the same open reading frame. The number of different clones isolated and sequenced containing each type of organisation is indicated in parentheses.

(a) Summary of constructs. pLEX (HIS) .DP-3 contains full length fusions of DP-3 α, β, γ and δ with the LexA DNA binding domain.

(b) β-galactosidase activity was measured in *S. cerevisiae* strain CTY-5d transformed with the indicated expression vectors.

(c) The indicated expression vectors were used to transform *S. cerevisiae* strain W303-1a carrying p4xWT CYC1 and β-galactosidase activity was measured. The results shown were derived from six independent colonies.

DISCLOSURE OF THE INVENTION

We have now surprisingly found that DP-3 exists as four isoforms encoded by a single gene. Processing events in the 5' region of DP-3 RNA determine whether translation begins at one of two potential initiation sites and alterations within the DP-3 coding sequence, which occur close to and within the DNA binding domain, generate another level of diversity. An analysis of DP-3 RNA suggests that, altogether, four distinct DP-3 proteins can be synthesized, $\alpha$, $\beta$, $\gamma$ and $\delta$. These DP-3 proteins co-operate with E2F family members in DNA binding activity and transcriptional activation.

Thus our characterisation of DP-3 indicates that it is a novel member of the DP family of proteins and that its RNA undergoes extensive alternative splicing. A sequence of 16 amino acid residues within the N-terminal region of the DNA binding domain, known as the E region, is one such region subject to the alternative splicing of DP-3 RNA. In the four DP-3 protein products which have been characterised, $\alpha$ and $\delta$ constitute E+ forms, whereas $\beta$ and $\gamma$ are E− variants. Although extensive sequence conservation is apparent across the DP protein family, a comparison of the known DP protein sequences indicated that they fall into two categories, being either E+ or E=; for example, DP-1 is an E− variant.

We have further defined a role for the E region by showing that its inclusion contributes to an alternatively spliced nuclear localization signal: specifically, E+ DP-3 proteins accumulate in nuclei whereas E⁻ proteins, including DP-1, fail to do so. Without the E region, DP proteins rely upon an alternative mechanism which involves an interaction with an appropriate E2F family member, for example E2F-1, for nuclear accumulation.

Thus, we have found an additional mechanism of control in regulating the activity of E2F mediated at the level of intracellular location. Specifically, our data show that two alternative mechanisms exist which control the nuclear accumulation of the DP/E2F heterodimer regulated, firstly, by alternative splicing and, secondly, subunit composition of the heterodimer. We show that the E region is encoded by an alternatively spliced exon which, together with an additional C− terminal extension, can confer efficient nuclear accumulation. The E region therefore contributes to a nuclear localization signal.

Thus, the DP-3 locus gives rise to RNA species which in turn result in at least four distinct DP-3 proteins with subtle differences in the length of the N-terminal region and organisation of internal domains. An analysis of the functional properties of these proteins found that the DP-3 proteins can co-operate with E2F-1 in DNA binding activity and transcriptional activation. The multiple products of the DP-3 locus and the variation in DP-3 proteins distinguish this member of the family from others isolated so far (Bandara et al., 1993; Girling et al., 1993; Helin et al., 1993; Krek et al., 1993; Girling et al., 1994).

Accordingly, the present invention provides a DP-3 polypeptide in substantially isolated form which is selected from the group consisting of:

(a) the sequence set out in SEQ ID NO:1 and SEQ ID NO:2, or a fragment or variant of said polypeptide which includes a functional E domain and retains the ability to form a functional transcription factor in association with E2F-1;

(b) the sequence set out in SEQ. ID NO:3 and SEQ ID NO:4, or a fragment or variant of said polypeptide which retains the ability to form a functional transcription factor in association with E2F-1;

(c) the sequence set out in SEQ. ID NO:5 and SEQ ID NO:6, or a fragment or variant of said polypeptide which includes a glutamine corresponding to Glu97 of SEQ. ID NO:5 and SEQ ID NO:6 and retains the ability to form a functional transcription factor in association with E2F-1;

(d) the sequence set out in SEQ. ID NO:7 and SEQ ID NO:8, or a fragment or variant of said polypeptide which includes a functional E domain and retains the ability to form a functional transcription factor in association with E2F-1.

Preferably, the polypeptide of claim of the invention is selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8

The invention further provides a nucleic acid encoding the polypeptide of the invention, and vectors, particularly expression vectors comprising such nucleic acid operably linked to a promoter.

The vectors may be introduced into a host cell to replicate the vector and to express a polypeptide of the invention by a method comprising:

i) providing a host cell carrying a expression vector of the invention with a promoter compatible with said host cell;

ii) growing said host cell under conditions to bring about expression of the polypeptide; and iii) recovering the polypeptide.

Polypeptides of the invention may be used in a screening method for identifying putative chemotherapeutic agents for the treatment of proliferative or viral disease which comprises:

(A) bringing into contact:
   (i) a DP-3 polypeptide according to the invention;
   (ii) an E2F polypeptide capable of forming a functional transcription factor in association with said DP-3 polypeptide; and
   (iii) a putative chemotherapeutic agent; under conditions in which the components (i) and (ii) in the absence of (iii) form a complex, and (B) measuring the extent to which component (iii) is able to disrupt or inhibit the activity of said complex.

The complex of (i) and (ii) may be measured by any suitable means, including for example its ability to bind an E2F DNA binding site in vitro, or by its ability to activate in vivo a promoter comprising an E2F binding site linked to a reporter gene. Such in vivo assays may be performed in a suitable host cell, including a yeast cell, insect cell or a mammalian cell.

The present invention further provides an assay for a putative antagonist of cell cycle progression which comprises:

a. expressing in a cell a protein comprising (i) the E region and sufficient C-terminal residues thereof of a DP-3 protein to provide a functional nuclear localisation signal (NLS) and (ii) a marker for nuclear localization; and b. determining the degree of nuclear localization in the presence and absence of said putative antagonist.

The protein defined in part "a" above will be referred to as the "protein comprising the E region" for the sake of brevity.

DETAILED DESCRIPTION OF THE INVENTION

A. Polypeptides.

Polypeptides of the invention include polypeptides in substantially isolated form which comprise the sequence set out in any one of SEQ ID NO:1, SEQ ID NO:2, SEQ ID NO:3, SEQ ID NO:4, SEQ ID NO:5, SEQ ID NO:6, SEQ ID NO:7 and SEQ ID NO:8, which represent, respectively, the α, β, γ and δ isoforms of DP-3. Polypeptides of the invention also include proteins comprising the E-region as defined above.

The term "substantially isolated form" will be understood to mean that the polypeptide may be mixed with carriers or diluents which will not interfere with the intended purpose of the polypeptide. A polypeptide of the invention may also be in a substantially purified form, in which case it will generally comprise the polypeptide in a preparation in which more than 90%, e.g. 95%, 98% or 99% of the polypeptide in the preparation is a polypeptide of the invention. Polypeptides of the invention may be modified for example by the addition of Histidine residues to assist their purification or by the addition of a signal sequence to promote their secretion from a cell.

Polypeptides further include variants of such sequences, including naturally occurring allelic variants and synthetic variants which are substantially homologous to said polypeptides. In this context, substantial homology is regarded as a sequence which has at least 90% amino acid homology (identity) overall to the DP-3 isoforms of the invention. Preferably, the variants have 95% amino acid identity and most preferably 98% identity.

Polypeptide variants also include other those encoding DP-3 isoform homologues from other species including animals such as mammals (e.g. rats or rabbits), and most preferably from primates, particularly humans.

Variants of isoforms of DP-3 include those which contain conserved substitutions which may be made according to Table 1, where amino acids on the same block in the second column and preferably in the same line in the third column may be substituted for each other:

TABLE 1

| ALIPHATIC | Non-polar | G A P |
| --- | --- | --- |
| | | I L V |
| | Polar - uncharged | C S T M |
| | | N Q |
| | Polar - charged | D E |
| | | K R |
| AROMATIC | | H F W Y |
| OTHER | | N Q D E |

A polypeptide of the invention may be labelled with a revealing label. The revealing label may be any suitable label which allows the polypeptide to be detected. Suitable labels include radioisotopes, e.g. $^{125}$I, enzymes, antibodies, polynucleotides and linkers such as biotin. Labelled polypeptides of the invention may be used in diagnostic procedures such as immunoassays in order to determine the amount of a polypeptide of the invention in a sample. This is of use in the mechanisms of cell proliferation which involve expression of DP-3 isoforms. Polypeptides or labelled polypeptides of the invention may also be used in serological or cell mediated immune assays for the detection of immune reactivity to said polypeptides in animals and humans using standard protocols.

A polypeptide or labelled polypeptide of the invention or fragment thereof may also be fixed to a solid phase, for example the surface of an immunoassay well or dipstick.

Such labelled and/or immobilized polypeptides may be packaged into kits in a suitable container along with suitable reagents, controls, instructions and the like.

Such polypeptides and kits may be used in methods of detection of antibodies to DP-3 isoform proteins or variants or species homologues thereof by immunoassay.

Immunoassay methods are well known in the art and will generally comprise:

(a) providing a polypeptide comprising an epitope bindable by an antibody against said protein;

(b) incubating a biological sample with said polypeptide under conditions which allow for the formation of an antibody-antigen complex; and (c) determining whether antibody-antigen complex comprising said polypeptide is formed.

Polypeptides of the invention may be may by synthetic means known in the art as such or, more usually, by recombinant means. Such means are well known in the art and examples of such are described below and in the accompanying examples.

The polypeptides of the invention may be introduced into the cell by in situ expression of the polypeptide from a recombinant expression vector (see below). The expression vector optionally carries an inducible promoter to control the expression of the polypeptide.

DP-3 polypeptides which include a functional E domain will be those with the E domain insert sequence shown at positions 103 to 119 inclusive of SEQ ID NO:1, or a variant of said sequence which still allows the polypeptide to retain an E-domain related function, such as the ability to localize the DP-3 protein to the nucleus. This may be determined by any suitable means, for example by immunofluorescence methods as described in the Examples. In general, such a variant will have no more than from 1 to 5, preferably from 1 to 3, deletions, insertions or substitutions (particularly conservative substitutions as defined above) of the E domain of SEQ ID NO:1.

Variants of the DP-3 polypeptides of the invention, including mammalian homologue variants, are those which retain the ability to form a functional transcription factor in association with E2F- 1. This may be determined by routine experimentation by those of skill in the art. A typical assay will comprise a reporter gene construct which contains one or more E2F binding sites operably linked to a reporter gene such as lacZ. The DP-3 variant will be brought into contact with E2F-1 and the reporter construct under conditions suitable for the formation of a heterodimer between a polypeptide of the sequence SEQ. ID. NO:1 and SEQ ID NO:2 and E2F-1. The conditions will be suitable for site dependent transcriptional activation to occur should a functional complex be formed.

Suitable conditions are described in, for example, Bandara et al, 1993; and Ormondroyd et al, 1995, the disclosures of which are incorporated herein by reference.

Fragments of DP-3 polypeptides may also be tested in an analogous manner for their ability to form such a functional transcription complex.

B. Assays.

(i) General Methods

Polypeptides of the invention are useful in studying the mechanisms of cell proliferation and for screening compounds which have the potential to disrupt the formation of complexes of a DP protein with an E2F protein which will consequently inhibit cell proliferation.

In addition, we have previously found that the first member of the DP family to be identified, DP-1, is regulated by phosphorylation during the cell cycle. In particular, DP-1 binds to DNA in the hypophosphorylated state. In other words, when DP-1 is phosphorylated, it does not have as great an affinity for DNA as it does when either not phosphorylated or hypophosphorylated. We believe similar regulation of DP-3 may also occur during the cell cycle and thus the growth of cell may be regulated by the phosphorylation of DP-1.

The present invention thus also relates to an assay for agents which prevent or inhibit the hypophosphorylation of DP-3 or which enhance the phosphorylation of DP-3. Such agents can be used to prevent or delay entry of the cell cycle into S phase from $G_1$. Antibodies against the regions of DP-3 which undergo a change in phosphorylation during the cell cycle may also be used in such assays, and to identify proliferating cells.

The present invention thus provides an assay for potential growth inhibiting agents which comprises:

(i) bringing the agent into contact with a cell; and
(ii) observing the phosphorylation state of a DP-3 polypeptide of the invention.

The invention also provides an agent obtainable from such an assay. The agent may be used in a method of controlling uncontrolled cell proliferation. Such a method may comprise administering to an individual with cells undergoing uncontrolled cell proliferation an effective amount of the agent.

In a simpler form, the assay of the invention may comprise:

(i) providing an extract of cells from cells which contains a DP-3 polypeptide in a hypophosphorylated state;
(ii) bringing the extract into contact with the agent; and
(iii) observing the phosphorylation state of said DP-3 polypeptide.

This assay can be used to screen agents which have the ability to activate the kinase which phosphorylates DP-3, thereby reducing its affinity for DNA.

The assay may also comprise:

(i) providing an extract of cells from a cell which contains a DP-3 polypeptide in a phosphorylated state;
(ii) bringing the extract into contact with the agent; and
(iii) observing the phosphorylation state of said DP-3 polypeptide.

This assay may be used to screen agents which have the ability to maintain DP-3 in a phosphorylated state or alternatively prevent hypophosphorylation of DP-3.

In the first of the above embodiments of the invention, the cell with which the agent is brought into contact may be any cell in which DP-3 is expressed. This includes mammalian (including human, primate and rodent) cells and amphibian cells (including *Xenopus* cells).

The cell may a cell which is maintained in in vitro culture. In conducting the assay, the cell may be maintained in a quiescent state (e.g. in $G_0$). This can be achieved by growing cells in a serum free medium. Techniques for achieving this are well known in the art and suitable media are commercially available. This will be desirable in that the assay may be conducted on a population of cells which are maintained in synchronous culture so that the effects of the agent in effecting the phosphorylation state of DP-1 at any particular point in the cell cycle may be determined. The cell may be a primary cell, a transformed cell or a tumour cell.

The DP-3 polypeptide may be the native DP-3 of the cell or may be expressed by a recombinant DNA construct within the cell. The expression may be transient from an extrachromosomal element or from a stably integrated recombinant DNA in the cell. The constructs will comprise a DNA encoding a DP-3 polypeptide operably linked to a promoter compatible with the host cell. Such constructs may be made using conventional recombinant DNA techniques such as those disclosed in Sambrook et al (Molecular Cloning: A Laboratory Manual, 1989).

In all aspects of the invention, the phosphorylation state of DP-3 may be measured by any suitable technique available to those of skill in the art.

For example, the mobility of DP-3 on a SDS/polyacrylamide gel is dependent on its state of phosphorylation. Thus electrophoresis of an extract from the cells which are undergoing an assay according to the invention followed by immunoblotting may be used to determine the relative amounts of phosphorylated and unphosphorylated DP-3 in a sample and thus the phosphorylation state of DP-3.

The DP-3 may also be assayed by growing cells prior to assay in a medium which includes a labelled phosphate group which may become attached to DP-3 via the natural processes in the cell. The amount of labelled DP-3 in the presence or absence of the agent can then be measured by for example immunoprecipitating DP-3 using an anti-DP-3 antibody and then measuring the amount of label precipitated. DP-3 antibodies may be obtained methods analogous to those of WO94/10307 which describe the production of antibodies against DP-1 and which is incorporated herein by reference.

Another method to assay the DP-3 is to measure its ability to form a complex with E2F-1 (or another member of the E2F family) and optionally to determine the ability of the complex to activate transcription. This may be done by reference to the techniques described above and in WO94/10307.

In a further embodiment of the invention, the candidate agent may be assayed using a fragment of DP-3 (reference to a fragment includes synthetic or recombinant peptides corresponding to such a fragment) which has been phosphorylated. In this embodiment of the invention, a cell, or an extract thereof, is brought into contact with the agent in the presence of the phosphorylated fragment and the amount of dephosphoylation of the fragment which occurs is measured.

The fragment of DP-3 is preferably derived from the C-terminal region of DP-3. For example, it may comprise a fragment of from 20 to 50 amino acids (e.g. 25, 30 or 40 amino acids) derived from a contiguous sequence within the final 100 (e.g. 90, 80, 60, 50, 40 or 30 amino acids of SEQ ID NO:1, SEQ ID NO:2,SEQ ID NO:3, SEQ ID NO:4, SEQ ID NO:5, SEQ ID NO:6, SEQ ID NO:7 and SEQ ID NO:8.

We have found that a monoclonal antibody raised against a synthetic peptide corresponding to residues 385–400 of DP-1 recognizes DP-1 in its hypophosphorylated state (since the synthetic peptide is unphosphorylated) but binds less well to DP-1 when phosphorylated. This indicates that hypophosphorylation of DP-1 occurs at least in part in this region of the protein. Fragments based on the corresponding region of DP-3 may find utility assays of the present invention.

The phosphorylation status of the peptide fragments of DP-3 may also be measured by the use of an antibody which recognises the unphosphorylated, but not phosphorylated peptide. Such an antibody may be made using standard techniques for the production of hybridomas, and used in the assay of the invention by first of all adding the labelled peptide and candidate agent to the cell or extract thereof, incubating the mixture obtained (typically for anywhere between 0.5 to 60, e.g. 1–30 or 5–15 minutes at between about 10–40, e.g. 20°, 25°, 30° or 37° C.) and then adding the antibody to the mixture to determine the amount of dephosphorylation of the peptide which has occurred. The antibody should be added in molar excess to the starting amount of peptide in order to bind all unlabelled peptide which has been produced.

Alternatively, the antibody may be used in an analogous manner to determine the amount of phosphorylation when the peptide is assayed in the presence of an extract containing an activity in which the kinase which phosphorylates DP-3 is present.

The amount of agent which may be used in the assay may vary over a wide range, depending upon factors such as its potential level of activity, toxicity or solubility. Typical concentrations of the agent when brought into contact with a cell or extract thereof will be from about 1 nM to 100 mM, eg from 10 nM to 10 mM.

Where the assay is performed using a fragment of DP-3, the amount of fragment will be in the range of from about 1 nM to 100 mM, eg from 10 nM to 10 mM.

Suitable candidate agents include peptide fragments of DP-3 (including such fragments produced by synthetic or recombinant means), including C-terminal fragments. Such fragments include those C-terminal fragments mentioned above. Agents which have activity in the assay can be refined and developed to produce higher activity agents by methods such as molecular modelling or peptide scanning.

The extract of cells for use in all embodiments of the invention are suitably extracts from the types of cells mentioned above, preferably obtained from cells in synchronous culture, and thus is in a defined stage of the cell cycle, e.g. $G_1$ or S. This includes cells transformed or transfected with a recombinant DNA encoding DP-3. The extracts may be obtained from cell which have been labelled with radioactive phosphate and the phosphorylation status of DP-3 may be measured in the manner described above for the first mentioned embodiment of the invention. Methods for preparing suitable extracts of cellular proteins are well known in the art.

The different isoforms of DP-3 suggest that DP-3 is involved in the regulation of the cell cycle in a number of different situations, for example where cells are undergoing differentiation or apoptosis. Thus increasing the level of one or more isoforms of DP-3 in a cell may be useful in directing cells to undergo differentiation or apoptosis. The increase may be achieved by, for example, increasing the level of expression of DP-3 or one of its isoforms, or by promoting the stability of DP-3 protein or mRNA in the cell.

Thus the present invention also provides an assay for a candidate positive effector of DP-3 expression or stability in a cell which comprises bringing the candidate effector into contact with a cell and observing the change in level of DP-3 expression.

The cell is preferably a mammalian cell, e.g murine or human. The cell may be a cell undergoing uncontrolled cell proliferation, e.g it may be a tumour cell, such as a lung, liver, colon, breast, ovary or brain cell. The cell will generally be grown in an in vitro culture system, conditions for which are well known in the art. The cell may also be in the form of a xenograft in a test animal, such as a nude mouse.

The level of expression of DP-3 may be oberved directly, e.g by northern anaylsis using a probe to detect DP-3 mRNA. Such a probe may be to a region of DP-3 common to all isoforms or specific to a subset, e.g. it may be an E-region isoform. A collection of probes may be used to determine if a change in the relative proportions of the isoforms has occured. The level of expression may also be determined by immunological means, by analogy to the methods described in the following examples.

The change in level of DP-3 expression may also be inferred where effects such as differentiation or apoptosis of the cell is observed.

Amounts of candidate effectors will vary depending upon the exact nature of the substance and the particular assay format used, but concentrations of agent similar to those mentioned above in connection with other assay formats can be used.

(ii) E-region assays

Assays which utilise the E region to identify antagonists of cell cycle progression may use any DP-3 E-region.

In one embodiment, the E region comprises the sequence:

S D R K R A R E F I D S D F S E (SEQ ID NO:9).

However, this E region is derived from the murine DP-3 gene and other E regions may be used, for example the human E region or other mammalian E regions. Other DP-3 genes may be obtained by routine cloning methods. For example, the human DP-3 gene may be cloned by probing a cDNA or genomic library with a nucleic acid probe derived from either a known human DP-gene (e.g. DP-1) and/or the murine DP-3 gene, and positive clones selected and sequenced for the human DP-3 gene. Similar techniques may be used for other mammalian DP-3 genes and will be readily apparent to those of skill in the art.

Comparison of the sequence of the sixteen amino acid residues within the E region to other previously defined NLSs suggests a closer resemblance to a bi-partite NLS rather than the NLS characteristic of SV40 large T antigen (Dingwall and Laskey, 1991). Although there is some similarity to the SV40 large T antigen-like NLS, neither the sequence nor the functional properties of the E region completely satisfy the requirements for this type of NLS (Boulikas, 1993; 1994). For example, the consensus core sequence for an SV40 large T-like motif is likely to consist of at least four arginine and lysine residues, whereas the cluster within the E region consists of three basic residues. Secondly, acidic residues are rarely included within the signal sequence, yet the E region cluster contains an aspartate residue embedded within it.

As described herein, the E region requires a number of C-terminal residues found in the DP-3 sequence in order to function as an NLS. Desirably, from 6 to 50, e.g 8 to 30 and preferably from 8 to 20 C-terminal residues are used.

Although assays of this aspect of the invention are preferably based upon naturally occurring E region sequences and associated C-terminal regions thereof sufficient to act as an NLS, these sequences may also be modified by substitution, deletion or insertion provided that the function of these sequences is substantially retained. The retention of function may be tested for in accordance with the description and examples herein.

For example, from 1 to 4 substitutions may be made and these are preferably conservative substitutions. Examples of conservative substitutions include those referred to in Table 1 above. Where deletions or insertions are made, these are preferably limited in number for example from 1 to 3 of each.

The cell in which the assay may be conducted is any suitable eukaryotic cell in which the E region functions as an NLS. Suitable cell types include yeast, insect or mammalian cells, e.g. primate cells such as COS7 cells.

In the assay according to the invention the marker for nuclear localization may be any polypeptide sequence which allows detection of the presence and location (i.e. cytoplasmic vs nuclear) of the protein comprising the E-region. Suitable markers include an antigenic determinant bindable by an antibody, an enzyme capable of causing a colour change to a substrate or a luciferase enzyme.

In a preferred embodiment, the marker comprises a transcription factor or subunit thereof, which transcription factor is capable of activating an indicator gene. This embodiment avoids the need for detailed examination of the cell to determine where the marker has located. In this embodiment the activation of transcription of the indicator gene will show that the E region has been located the protein in the nucleus.

For example, in a preferred embodiment of the invention the protein may comprise a heterologous DNA binding domain such as that of the yeast transcription factor GAL 4. The GAL 4 transcription factor comprises two functional domains. These domains are the DNA binding domain (DBD) and the transcriptional activation domain (TAD). By fusing the E region to one of those domains and expressing the other domain in the cell, a functional GAL 4 transcription factor is restored only when two proteins enter the nucleus and interact. Thus, interaction of the proteins may be measured by the use of an indicator gene linked to a CAL 4 DNA binding site which is capable of activating transcription of said reporter gene. This assay format is described by Fields and Song, 1989, Nature 340; 245–246.

The indicator gene may comprise, for example, chloramphenicol acetyl transferase (CAT) or a luciferase.

In any format, the assay may be used to screen peptides which antagonise the function of the E region in DP-3. Such antagonists will be useful either in themselves as potential regulators of cell proliferation or as models for rational drug design, e.g. by modelling the tertiary structure of the antagonist and devising chemical analogues which mimic the structure.

Candidate antagonists include peptides comprising all or part of a sequence which is from 60 to 100% homologous (identical) to a portion of the E region of the same length.

The amount of a putative antagonist which may be screened in the assay of the invention desirably will be selected to be a concentration which is within 100 fold (above or below) the amount of E region-containing protein in the cell.

The assay of the invention may be conducted using transient expression vectors or stably transfected cells. In either case, the protein comprising the E region will be encoded by nucleic acid (preferably DNA) and said nucleic acid will be operably linked to a promoter which is functional in the host cell. The promoter and nucleic acid encoding the protein comprising the E region will usually be part of a vector construct which may also contain signals for termination of transcription, a selectable marker and/or origins of replication functional in the host cell and/or in another cell type (e.g. E.coli) so that the vector may be manipulated and grown in the other cell type.

Where the E region sequence contains substitutions, deletions or insertions as described above the alterations to the sequence may be made by manipulation of the nucleic acid sequence to alter the relevant codon(s) . This can be achieved by a number of well known standard techniques, e.g. site directed mutagenesis.

Various vectors of this type are described in the Examples herein, and further vectors may be made by those of skill in the art in accordance with routine practice in molecular biology.

In a separate embodiment, the invention also provides a method of directing expression of a protein in a cell to the nucleus which comprises modifying said protein such that is comprises the E region and sufficient C-terminal residues thereof of a DP-3 protein to provide a functional nuclear localisation signal (NLS).

Such a method may be used to modify a DP-protein which does not normally comprise an E region so that the DP-protein (e.g. DP-1 or DP-2 does localise to the nucleus. This can be used to study the function of such DP proteins. These proteins are novel and thus form a further aspect of the invention.

Modification of such proteins will usually be achieved through the use of recombinant DNA techniques, e.g. using nucleic acid encoding the E region sequence and splicing it to or into nucleic acid encoding the protein of interest. The recombinant nucleic acid may be introduced into an expression vector in a manner analogous to that described above and the vector introduced into a suitable host cell, e.g. a host cell in which a promoter operably linked to the recombinant DNA coding sequence is capable of driving expression of the DNA. Suitable cell types include those described above.

In a further embodiment of the invention, the finding that DP proteins such as DP-1 lack an NLS indicate that the complex of such DP proteins with an E2F (such as E2F-1) are localised in the nucleus by the presence of an NLS on the E2F protein. The DP-3 NLS is not homologous to the E2F NLS. Thus the E2F NLS forms a further target for antagonists of nuclear localisation of the DP/E2F complex, particularly complexes such as DP-1/E2F-1 which do not comprise an E region.

Accordingly the present invention also comprises an assay for a putative antagonist of cell cycle progression which comprises:

a. expressing in a cell (i) an E– DP transcription factor or a portion thereof sufficient to form a hetrodimer with an E2F transcription factor and (ii) an E2F transcription factor or portion thereof sufficient to form a heterodimer with the DP transcription factor or portion thereof and direct localisation of said heterodimer to the nucleus; and b. determining the degree of nuclear localization in the presence and absence of said putative antagonist.

The assay may be performed under conditions and within cell types as described above for the assay of the E region antagonists.

In this assay, a preferred DP transcription factor is DP-1, particularly mammalian DP-1, e.g. rodent or primate, e.g. human. The sequences of human and mouse DP-1 are shown as SEQ ID NO:10 and SEQ ID NO:11 repectively. A preferred E2F is E2F-1, particularly mammalian E2F-1, e.g. rodent or primate, e.g. human. The sequence of human E2F-1 is shown as SEQ ID NO:12 and SEQ ID NO:13.

C. Nucleic acid and vectors.

Nucleic acids of the invention may comprise DNA or RNA. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or lifespan of polynucleotides of the invention.

Polynucleotides of the invention encoding the polypeptides of SEQ ID NO:1, SEQ ID NO:2,SEQ ID NO:3, SEQ ID NO:4, SEQ ID NO:5, SEQ ID NO:6, SEQ ID NO:7 and SEQ ID NO:8 will be preferably at least 70%, preferably at least 80 or 90%, more preferably at least 95% and most preferably >at least 98 or 99% homologous to the DNAs of SEQ ID NO:1, SEQ ID NO:2,SEQ ID NO:3, SEQ ID NO:4, SEQ ID NO:5, SEQ ID NO:6, SEQ ID NO:7 and SEQ ID NO:8 respectively. However the redundancy of the genetic code will allow sequence variation to occur which will not result in a change of the polypeptide sequence of SEQ ID NO:1, SEQ ID NO:2,SEQ ID NO:3, SEQ ID NO:4, SEQ ID NO:5, SEQ ID NO:6, SEQ ID NO:7 and SEQ ID NO:8. However, where variants of the said polypeptides of the invention are to be obtained, this is conveniently achieved by altering the sequence of the DNA sequence of any one of SEQ ID NO:1, SEQ ID NO:2,SEQ ID NO:3, SEQ ID NO:4, SEQ ID NO:5, SEQ ID NO:6, SEQ ID NO:7 and SEQ ID NO:8 to bring about a change in the translation of the open reading frames thereof.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length.

Polynucleotides such as a DNA polynucleotide and primers according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15–30 nucleotides) to a region of the DP-3 mRNA or genomic sequence encoding the mRNA which it is desired to clone, bringing the primers into contact with mRNA or cDNA obtained from a human cell (e.g. a spleen, heart, liver, thymus or brain cell), performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the DP-3 sequences described herein. Genomic clones containing the DP-3 gene and its introns and promoter regions may also be obtained in an analogous manner, starting with genomic DNA from a human cell, e.g. a liver cell.

Although in general the techniques mentioned herein are well known in the art, reference may be made in particular to Sambrook et al (Molecular Cloning: A Laboratory Manual, 1989).

Polynucleotides which are not 100% homologous to the sequences of the present invention but fall within the scope of the invention can be obtained in a number of ways.

Other murine variants of the DP-3 sequence described herein may be obtained for example by probing cDNA or genomic DNA libraries made from murine tissue.

In addition, other animal, particularly mammalian (e.g. rats or rabbits), more particularly primate including human, homologues of DP-3 may be obtained. Such sequences may be obtained by probing cDNA libraries made from dividing cells or tissues or genomic DNA libraries from other animal species, and probing such libraries with probes comprising all or part of any one of Seq. ID. Nos. 1 to 4 under conditions of medium to high stringency (for example 0.03M sodium chloride and 0.03M sodium citrate at from about 50° C. to about 60° C.).

Allelic variants and species homologues may also be obtained using degenerate PCR which will use primers designed to target sequences within the variants and homologues encoding conserved amino acid sequences. Conserved sequences can be predicted from aligning the DP-3 amino acid sequence with that of DP-1 and DP-2 (see Girling et al, 1994). The primers will contain one or more degenerate positions and will be used at stringency conditions lower than those used for cloning sequences with single sequence primers against known sequences.

Alternatively, such polynucleotides may be obtained by site directed mutagenesis of the DP-3 sequences or allelic variants thereof. This may be useful where f or example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides. F urth er changes may be desirable to represent particular coding changes found in DP-3 which are required to provide, for example, conservative substitutions.

Nucleic acid of the invention may be single or double stranded polynucleotides.

Polynucleotides or primers of the invention may carry a revealing label. Suitable labels include radioisotopes such as $^{32}P$ or $^{35}S$, enzyme labels , o r other protein labels such as biotin. Such labels may be added to polynucleotides or primers of the invention and may be detected u sing by techniques known per se.

Polynucleotides or primers of the invention or fragments thereof labelled or unlabelled may be used by a person skilled in the art in nucleic acid-based tests for detecting or sequencing DP-3 in the human or animal body. In the case of detecting, this may be qualitative and/or quantitative.

Such tests for detecting generally comprise bringing a human or animal body sample containing DNA or RNA into contact with a probe comprising a polynucleotide or primer of the invention under hybridizing conditions and detecting any duplex formed between the probe and nucleic acid in the sample. Such detection may be achieved using techniques such as PCR or by immobilizing the probe on a solid support, removing nucleic acid in the sample which is not hybridized to the probe, and then detecting nucleic acid which has hybridized to the probe. Alternatively, the sample nucleic acid may be immobilized on a solid support, and the amount of probe bound to such a support can be detected. Suitable assay methods of this any other formats can be found in for example WO89/03891 and WO90/13667.

The primers of the invention may conveniently be packaged in the form of a test kit in a suitable container. In such kits the probe may be bound to a solid support where the assay format for which the kit is designed requires such binding. The kit may also contain suitable reagents for treating the sample to be probed, hybridizing the probe to nucleic acid in the sample, control reagents, instructions, and the like.

D. Vectors.

Nucleic acid polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

E. Expression Vectors.

Preferably, a polynucleotide of the invention in a vector is operably linked to a control sequence which is capable of providing for the expression of the coding sequence by the host cell, i.e. the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Such vectors may be transformed into a suitable host cell as described above to provide for expression of a polypeptide of the invention. Thus, in a further aspect the invention provides a process for preparing polypeptides according to the invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo, for example in a method of gene therapy.

A further embodiment of the invention provides host cells transformed or transfected with the vectors for the replication and expression of polynucleotides of the invention. The cells will be chosen to be compatible with the said vector and may for example be bacterial, yeast, insect or mammalian.

Polynucleotides according to the invention may also be inserted into the vectors described above in an antisense orientation in order to provide for the production of antisense RNA. Antiserise RNA or other antisense polynucleotides may also be produced by synthetic means. Such antisense polynucleotides may be used in a method of controlling the levels of DP-3 or its variants or species homologues.

Promoters and other expression regulation signals may be selected to be compatible with the host cell for which the expression vector is designed. For example, yeast promoters include S. cerevisiae GAL4 and ADH promoters, S. pombe nmt1 and adh promoter. Mammalian promoters include the metallothionein promoter which is can be included in response to heavy metals such as cadmium. Viral promoters such as the SV40 large T antigen promoter or adenovirus promoters may also be used. All these promoters are readily available in the art.

F. Expression of DP-3 polypeptides.

Expression vectors of the invention may be used to obtain polypeptides of the invention. Methods of culturing host cells carrying expression vectors such as those carrying nucleic acid encoding a DP-3 protein described above are well known in the art and may be applied to the present invention. The DP-3 polypeptide produced may be recovered and purified by any convenient technique known to a person of skill in the art. Such techniques include preparative chromatographic techniques such as HPLC and antibody affinity chromatography methods.

In situations where DP-3 polypeptides are produced in in vivo assay systems, such as those described in Bandara et al, 1994, it may not be necessary or desirable to isolate the DP-3 polypeptide produced.

G. Summary.

Our analysis of DP-3 has defined four discrete forms of DP-3 RNA which arise through RNA processing, the most probable mechanism being alternative splicing. This is the first example of this level of control in the DP and E2F family members. A focus for these processing events exists in the 5' region of DP-3 RNA, where four different splicing arrangements were resolved which influence whether translation could theoretically begin at one of two potential initiating codons. In one species of DP-3 RNA, referred to as type II, translation can initiate at M1, whereas in types I, III and IV translation from M1 would meet several in frame stop codons, and thus translation through the DP-3 coding sequence could only initiate from the downstream site at M2. Initiation at M1 adds 61 residues to the N-terminus of DP-3 and results in synthesis of the $\alpha$ protein, whereas initiation at M2 would give rise to the $\beta$, $\gamma$ and $\delta$ forms of DP-3. Presently, we cannot rule out that other 5' end organisations which have not as yet been characterised exist; such 5' ends may be determined based on the work described herein.

The variety of organisations defined at the 5' end of DP-3 RNA has interesting implications since a preponderance of genes involved with growth control (proto-oncogenes and growth factors for example) also contain numerous translation initiation codons and associated open reading frames in 5' leader sequences (Kozak, 1987) which, in some cases, can regulate the utilization of downstream reading frames (Geballe and Morris, 1994). Notable examples include the yeast GCN4 gene the translation of which is regulated by a series of small upstream open reading frames (Altmann and Trachsel, 1993), and the adenosylmethionine decarboxylase gene where an upstream six codon open reading frame represses downstream translation in normal T cells (Hill and Morris, 1993). It will be interesting to understand the functional significance of these DP-3 5' organisations and their role, if any, in translational control.

We have yet to uncover functional differences between DP-3 proteins where translation initiates at M1 (that is $\alpha$) and M2 ($\beta$, $\gamma$ or $\delta$). However, we note that several potential cdk phosphorylation sites are located between M1 and M2, and that cdk-dependent phosphorylation of DP-1 has previously been implicated in the regulation of the DP-1/E2F-1 heterodimer (Dynlacht et al., 1994; Krek et al., 1994). It is thus possible that the additional cdk sites located in DP-3 a confer additional cdk regulation.

There are several examples of eukaryotic genes which utilize more than one in-frame initiation codon where the length of the N-terminal region has significant functional consequences. For example, the transcription factor LAP has an alternative product known as LIP which initiates at a codon further downstream (Descombes and Schibler, 1991).

Although LAP and LIP contain a common dimerization domain, they differ in the presence of a transcriptional activation domain which results in LIP forming inactive homodimers or heterodimers with LAP (Descombes and Schibler, 1991).

In addition to the organisations at the 5' end, three species of RNA were defined with coding sequence modification, resulting in the insertion of 16 amino acid residues (the E region) or a single glutamine residue at position 97. Both DP-3 α and δ contain the E region whereas γ has the additional glutamine but not the E region; neither are present in δ. The ratio of glutamine-plus to glutamine-minus DP-3 RNA was found to be similar in a variety of tissues, and since γ is the only form of DP-3 known to be glutamine-plus, this result is consistent with the idea that DP-3 γ is constitutively expressed. Furthermore, an analysis of DP-3 RNA over the E region suggested a similar ratio of E region-plus to E region-minus RNA. Since the two forms of DP-3 which lack the E region are β and γ these results, combined with the implication from the previous analysis, suggest that DP-3 β is constitutively expressed. Overall, therefore, the RNAs which give rise to DP-3 β and γ may be constitutively expressed but this conclusion has an inherent caveat since we may not have characterised all species of DP-3 RNA which encode glutamine-plus or E region-minus DP-3.

When assayed as a heterodimer the E2F-1 subtle differences in the activities of the DP-3 proteins were apparent, notably in the yeast E2F-site activation assay (FIG. 3) and DNA binding assay. Given that the alterations in DP-3 protein sequence occur close to or within the DNA binding domain then such results may have been anticipated. Interestingly, a somewhat analogous situation has been documented for a member of the POU domain gene family where RNA processing at the level of alternative splicing generates I-POU, or twin of I-POU (Treacy et al., 1992). Both proteins possess distinct transcription properties due to a small alteration (two residues) in the POU DNA binding domain.

The insertion of a glutamine residue at position 97 disrupts a hypothetical casein kinase II phosphorylation site and, if this site were to be phosphorylated in physiological conditions, it is possible that it may influence protein activity and thus be responsible for some of the differences observed in these assays. In contrast to the disruption of a phosphorylation site by glutamine 97, the insertion of the E region introduces a number of hypothetical phosphorylation sites into α and δ proteins. There are many examples of transcription factors where phosphorylation influences activity (Hill and Treisman, 1995) and it will be interesting to determine the role, if any, of these changes in the regulation of DP-3.

In considering the relevance of DP-3, we note that in many cell types DP-1 appears to be the predominant DP family member in physiological DRTF1/E2F (Girling et al., 1993; Bandara et al., 1993; 1994). It is possible that DP-3 proteins are rare components of DRTF1/E2F or, alternatively, regulate E2F site- dependent transcription in physiological conditions where DP-1 does not play a major role.

To summarise, this analysis of DP-3 highlights another potential level for the control of E2F site transcription which differs from the previously documented regulation mediated by the physical association of pocket proteins with DP/E2F heterodimer and interaction with cyclins. The present invention has, in addition, uncovered a new level through which the activity of the DP component of DRTF1/E2F may be regulated through RNA processing events. Understanding the physiological roles of the different DP-3 proteins is thus likely to yield important insights into cell cycle control.

The following examples are provided to illustrate the invention in a non-limiting manner.

EXAMPLE 1

Isolation of DP-3 and characterisation of DP-3 variants.

Initially, cDNA clones encoding DP-3 were obtained by RT-PCR from murine brain mRNA using degenerate primers derived from the DNA sequence encoding the DEF box, the region in DP family members which contains the greatest level of similarity with E2F family members (Girling et al., 1993; 1994; Lam and La Thangue, 1994).

From twenty independent cDNA clones sequenced, eighteen contained DP-1 whilst two others represented novel sequence which displayed a high level of similarity to the other DP proteins, DP-1 and DP-2 (Girling et al., 1993; 1994), and thus represented a new member of the DP family. In keeping with the designation for previously isolated DP proteins as DP-1 and DP-2, we refer to the protein encoded by these clones as DP-3.

Probing an F9 EC cDNA library at high stringency allowed the isolation of two independent cDNA clones containing larger inserts. About $10^6$ p.f.u. of an oligo dT primed F9 EC library in γ-ZAP were transferred onto Hybond N (Amersham International) and hybridized at 68° C. with a $^{32}P$ labelled excised PCR fragment corresponding to DP-3 DNA. Filters were washed at high stringency and exposed to Kodak X-OMAT AR film. Two hybridising clones were isolated which were excised in vivo and sequenced using a Sequenase version 2.0 kit (USB).

After in vivo excision and DNA sequencing, the two clones (designated pl-i and pl-2) were found to contain inserts of 1.4 and 2.4kb respectively. The larger of the two, pl-1, contained more 3' untranslated sequence than pl-2 but did not extend as far 5'; the sequence of pl-2 is shown in SEQ ID NO:5. At this stage in the characterisation of DP-3, we noticed that a CAG codon was present at nucleotide position 523 in the pl-2 coding sequence (residue no. 97 in SEQ ID NO:5) which was not present in the initial cDNA fragment isolated from murine brain RNA.

In the pl-2 cDNA clone, in frame stop codons precede the first potential initiating methionine, M2. However, a comparison of the conceptual protein sequence of DP-3 (pl-2) with DP-1 revealed significant similarity further upstream of M2, suggesting that this region of the DP-3 RNA may, in certain circumstances, be translated. To investigate this possibility, RT-PCR was undertaken using a primer representing the most 5' sequence of pl-2 together with one derived from sequence just upstream of M2 using cDNA derived from brain and kidney RNA.

RNA was isolated from adult CBAN mouse tissues and F9 EC cells using Tri Reagent (MRC, Inc). About 1 µg of total RNA was incubated at 42° C. with a 100 ng of a DP-3 specific primer downstream from P2 and P3 and 1 U of AMV reverse transcriptase (Superscript, BRL) in the manufacturers' buffer. After 1 h, the reaction volume was increased to 100 µl with water and 1–5 µl used in a PCR reaction. Products were digested with restriction enzymes and cloned into pbluescript (pBS, Stratagene) for sequencing.

The PCR products, ranging in size from 200 to 300 base pairs, were cloned, subsequently sequenced and found to include several variations in the organisation of the 5' region (shown schematically in FIG. 1); in total seventeen different cDNA clones were sequenced. The organisation of the original cDNA clone isolated from an F9 EC library, pl-2, is represented as type I. In one alternative organisation, referred to as type II, an additional 80 nucleotides were defined (indicated as segment 3 in FIG. 1). The inclusion of segment 3 moves another potential initiating methionine designated M1 (located within segment 2), into the same coding frame as M2, thus adding 61 amino acid residues to the amino terminal end of DP-3 (FIG. 2); stop codons located upstream of M1 would prevent read through translation. Two further variations were characterised, referred to as type III and IV. In type IV, the addition of 60 nucleotides (indicated as segment 4 in FIG. 1) introduces a stop codon in frame with M1. In contrast, in type III the RNA sequence containing M1 is not present, that is, segment 2 is absent (FIG. 1). In types I, III and IV, the first in frame and potential initiating methionine is M2 suggesting that translation begins at the same position in the three different 5' organisations. Altogether, we isolated and sequenced cDNA clones with a type I organisation four times, type II seven times, type III four times and type IV once.

Figure 2:
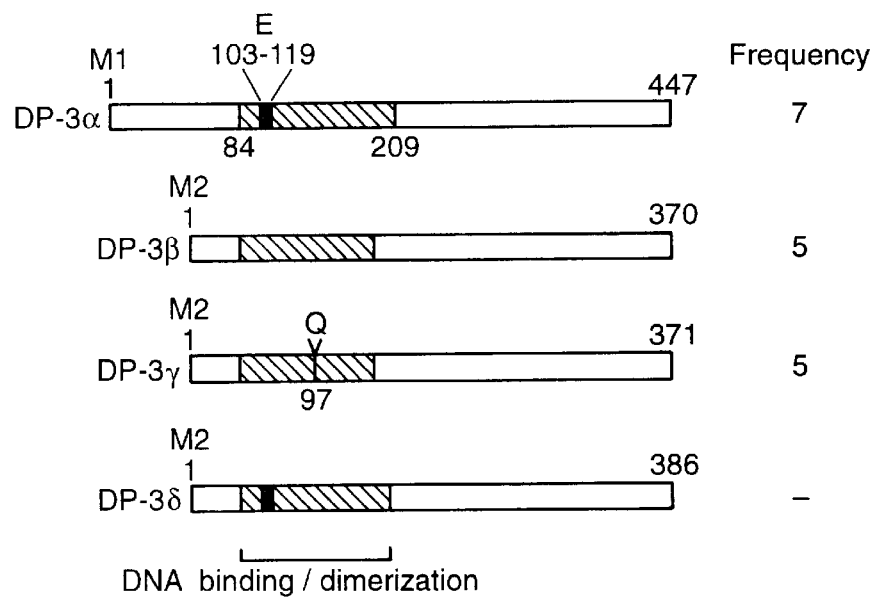
FIG. 2 shows a schematic representation of the forms of DP3 protein, α, β, γ and δ.

In order to assess the relationship between these different organisations of the DP-3 RNA and the presence or absence of the glutamine codon at residue position 97, further RT-PCR was carried out with primers P1 and P3, P1 being derived from the 5' region and P3 occurring downstream of the glutamine codon. Further sequence analysis of the PCR cDNA products revealed another level of variation since some clones contained additional DNA sequence which would, in the mature DP-3 protein, result in the insertion of 16 residues (FIG. 2); this region is referred to as the E region for extra coding region. The forms of the DP-3 protein encoded by the various cDNAs in the pool of clones sequenced are shown in FIG. 2. Overall, we isolated and characterised cDNAs containing the extra glutamine codon five times, the E region seven times and clones without the glutamine codon and the E region five times. This analysis of DP-3 cDNAs indicated that all clones where translation can initiate from M1 (that is, the type II organisation) contained the E region but lacked the additional glutamine codon; we refer to this species of DP-3 as a. The α species is that shown in SEQ ID. NO:1 and SEQ ID NO:2.

In the other types where initiation at M1 cannot occur, but rather at M2, two different organisations were characterised; β (SEQ ID NO:3 and SEQ ID NO:4) which lacks the glutamine residue and E region, and γ (SEQ ID NO:7 and SEQ ID NO:6 containing the glutamine residue but not the E region.

The nature of DP-3 δ (SEQ ID NO:7 and SEQ ID NO:8), which contains the E region but lacks the glutamine was predicted from the data derived from the RNA protection assays (discussed later). In this analysis the β cDNA clones correlated with type I or type III organisations (one and four clones respectively) and γ clones with type I or type IV organisations (three and one clone respectively).

Sequence comparison of DP-3 indicated a high degree of similarity with other members of the DP family, notably DP-1 and DP-2; Girling et al., 1993; Girling et al., 1994). Of potential interest is the fact that the DP-3 M1 initiating methionine (present in DP-3 α) and the corresponding protein sequence between M1 and M2 aligns with the initiating methionine of DP-1, and the M2 initiating methionine (present in DP-3 β, γ and δ) is in the same position as the initiating methionine in DP-2. The E region in DP-3 α and DP-3 δ has 14 out of 16 residues in common with a similarly positioned region in DP-2 which is not apparent in DP-1.

Overall, the murine DP-3 α protein is 69% identical to murine DP-1 and 72% identical to Xenopus laevis DP-2. Since the level of identity between potential DP-1 homologues from different species is greater than the level of identity between murine DP-1 and DP- 3, we feel that it is likely that DP-3 represents a novel member of the DP family of proteins rather than the murine DP-2 homologue; for example, murine and X.laevis DP-1 are 92% identical (Girling et al., 1994), compared to murine DP-3 and X.laevis DP-2, which show 72% identity. The domains previously noted in DP proteins are particularly well conserved in DP-3. Notably, the DEF box, DCB1 and DCB2 are the regions of DP-3 most conserved with other members of the family (FIG. 2).

EXAMPLE 2

Expression of DP-3 RNA

The results of the RT-PCR cloning and analysis of DP-3 cDNA clones revealed the existence of multiple 5' ends and alterations in the coding sequence. To determine whether these clones represent physiological derivatives of the DP-3 locus we carried out RNase protection analysis on cellular RNA with probes spanning the regions of interest. The analysis was performed with RNA from different mouse tissues to assess if there are tissue influences on the regulation of DP-3.

Initially, we assessed the levels of the various 5' organisations defined in the DP-3 cDNA analysis using probes derived from type I, type II and type III 5'-ends. These data suggested that their distribution is tissue-restricted. For example, kidney and brain contain the same amount of the type I organisation, although the amount of type II was significantly greater in kidney than in brain. These RNA protection assays allowed us to conclude that the various arrangements of 5' ends of DP-3 RNA are physiologically relevant and tissue-restricted. The expression pattern of type IV has yet to be resolved.

Next, we studied the expression of RNAs containing or lacking the CAG codon encoding the glutamine at residue position 97 using a probe derived from DP-3 γ which contained the CAG codon. These results indicated that specific DP-3 RNA was present in all the mouse tissues analysed although the abundance varied from tissue to tissue. Thus, DP-3 RNA was present at a greater level in spleen and heart compared to liver, thymus and brain. The results also indicated that both species of RNA, CAG plus and minus, are expressed in all the tissues examined since three fragments (predicted from CAG plus and minus RNA species) were detected in the RNase protection assay. A quantification of the protected fragments established that the more abundant RNA species lacked the CAG sequence (about 80% of the total RNA), although the ratio of both species of RNAs remained similar in the RNA preparations analysed. This result is in agreement with the majority of the cDNA clones isolated from brain or kidney lacking the glutamine codon.

The distribution of RNAs containing the E region was next examined with a probe derived from a brain DP-3 clone cDNA containing this E region sequence but lacking the CAG codon. Protected fragments of 290 nucleotides together with one of 202 nucleotides were detected in all the tissues analyzed. These tissues included liver, testis, spleen, thymus, heart, lung, brain, kidney and muscle tissues, as well as F9 EC cells.

None of the CAG-containing forms that were revealed in the previous analysis were apparent in this analysis, probably because of the inability of ribonucleases to recognize quantitatively the small mismatch in this probe.

It should be noted that when RNA probes for the coding region of DP-3 were analysed, we observed that DP-3 RNA was highly abundant in spleen. However, for the 5'-end organisations identified, spleen is the tissue with lowest amount of any of the different 5'-ends. It is possible, therefore, that at least one other 5' end arrangement exists in spleen RNA which we have not yet analysed. The presence of DP-3 RNA with a δ organisation was implied from the high level of DP-3 RNA from spleen containing the E region and the low levels of the type II organisation in spleen RNA.

EXAMPLE 3

Functional analysis of DP-3 proteins

The analysis of DP-3 cDNA clones and RNA levels suggested that at least four distinct DP-3 proteins, α, β, γ and δ, can be synthesized (FIG. 2). To explore the possibility that these proteins possess distinct functional properties, we assessed their activities in a number of relevant assays. Because some of the variation in the DP-3 proteins occurs in, or close to the DNA binding region and dimerization domain (Bandara et al., 1993; 1994), initially we assessed whether this variation in protein sequence influenced their ability to form heterodimers with E2F family members. For this, we used the yeast two-hybrid assay (Fields and Song, 1989) which has been used previously to demonstrate an interaction between DP-1 and different E2F family members in the absence of DNA binding (Bandara et al., 1993). In this assay, DNA binding specificity was provided by the LexA DNA binding domain fused to the DP-3 coding sequence and transcriptional activation by the Gal4 activation domain, GAD, fused to E2F-1 (FIG. 3a).

The yeast two-hybrid expression plasmids used are pLEX (HIS) which contains the complete LexA coding sequence (Buck et al., 1995), pGAD.L6 which contains the Gal4 transcription activating domain (Bandara et al., 1993), PLEX(HIS).DP1 which contains the mouse DP-1 fused to the C-terminus of the LexA coding sequence and pGAD.E2F-1 which contains the human E2F-1 downstream of the Gal4 activation domain (Bandara et al., 1993).

The different forms of DP-3 were expressed as fusions to the LexA DNA binding domain. For that, full length DP-3 α, β, γ, and δ were cloned into pLEX(HIS). The cloning junctions were sequenced to confirm that the fusions were correct.

The *Saccharomyces cerevisiae* yeast strain CTY10-5d (Cheng-Tien Chen and Rolf Sternglanz; Mata ade2 trp1-901 leu2-3,112 his3-200 gal4 gal80 URA3::lexAop-lacZ) was used for the yeast interaction assay, and the yeast strain W3031a (Thomas and Rothestein, 1989; Mata ade2-1 tripl-1 leu2-3, 112 his3-11, 15 ura3) carrying the reporter plasmid p4xWT CYC1 (Bandara et al., 1993) in which the lacZ gene is under the control of the adenovirus E2a promoter E2F site, was used for the yeast E2F site-dependent transcription assay.

Yeast transformations and β gal assays were performed as described (Bandara et al., 1993). At least three independent transformant colonies were assayed.

The LexA-DP-3 fusion proteins were not able to induce β-galactosidase activity from the LexA binding site reporter (FIG. 3b). However, a great increase in activity was apparent when any of the LexA-DP-3 hybrids was co-expressed with GAD-E2F-1 (FIG. 3b). We conclude that DP-3 α, β, γ and δ functionally interact with the E2F family member E2F-1. Since the level of activation was similar when each of the different DP-3 hybrids were co-expressed with E2F-1, the variation in protein sequence in DP-3 does not, in the conditions of this assay, overtly affect the formation of DP-3/E2F-1 heterodimers.

We next assessed the transcription properties of the DP-3/E2F-1 heterodimers using a yeast assay which measures the transcriptional activity of the E2F site reporter, p4xWT CYC1 (FIG. 3a). Previous studies have shown that DP-1 together with E2F family members co-operate in the E2F site-dependant transcriptional activation of this reporter construct (Bandara et al., 1993). Thus, we performed a similar analysis of the DP-3 proteins (FIG. 3c). Although there was a slight increase in activity with GAD-E2F-1 alone, in the presence of both E2F-1 and DP-3 hybrid proteins much greater activity was apparent (FIG. 3c). All the DP-3 hybrid proteins were capable of co-operating with the E2F-1 hybrid. Furthermore, and in contrast to the previous dimerization assay (FIG. 3b), significant differences were apparent between the activities of the DP-3 proteins. For example, the α hybrid was least efficient at co-operating with E2F-1, whereas γ possessed the greatest level of activity (FIG. 3c). We conclude from these data that generic DP-3 co-operates with E2F-1 but, importantly, that individual DP-3 proteins differ in the efficiency of co-operation.

EXAMPLE 4

DNA binding properties of DP-3 α, β, γ and δ

To investigate the DNA binding properties of the DP-3 proteins each coding sequence was expressed and purified as a GST fusion protein. GST E2F-1 has been described (Bandara et al., 1993) and GST DP-3 was made in an analogous manner. GST fusion proteins were purified according to Smith and Johnson (1988) and concentrations estimated by Coomassie staining.

After purification the DNA binding activity of each protein was assessed in the context of a heterodimer with E2F-1 by gel retardation in which the level of DP-3 protein was titrated into the DNA binding reaction with a constant amount of E2F-1. Gel retardation assays were performed using an oligonucleotide consisting of the distal E2F binding site in the adenovirus E2a promoter (nucleotides −71 to −50) as described previously (La Thangue et al., 1990).

In these conditions, DP-3 α, γ and δ behaved in a similar fashion since the quantitative induction of E2F site DNA binding activity with each protein followed a similar trend. The characteristics of the DNA binding activity obtained with DP-3 β were, however, significantly different; it efficiently co-operated at the low end of the titration but interfered with DNA binding activity at higher concentration. We conclude that there are subtle but significant differences in the DNA binding properties of the DP-3 proteins. Since there was little difference in the ability of DP-3 α, β, γ or δ to dimerize with E2F-1 (FIG. 3b), the different DNA binding properties are unlikely to be influenced by DP-3 dimerization.

EXAMPLE 5

The proteins encoded by the spliced variants of DP-3 have distinct intracellular distributions The DP-3 gene gives rise to a number of distinct proteins resulting from alternative splicing of its RNA (Ormondroyd et al., 1995). Since the DNA binding and transcription activation properties of the DP-3 variants, referred to as α, β, γ and δ, are not significantly different (Ormondroyd et al., 1995) we considered that the variation within the DP-3 coding sequence may influence other properties of the proteins, such as their biochemical properties. We therefore compared the biochemical extraction properties of β and δ, which constitute E– and E+ forms respectively, after sequential treatment with increasing salt concentration and monitoring the levels of protein extracted from transfected COS7 cells.

COS7 cells were trasfected with plasmids carrying the full length coding sequences of DP-3 α, β, γ and δ (Ormondroyd et al., 1995) which were cloned into pG4mpoliII (Webster et al., 1989) under the control of the SV40 early promoter. pG4DP-3αΔE mutant was constructed by substituting a Bsg1 fragment from DP-3β (E-minus) into DP-3α. A number of other vectors made in connection with other examples are descirbed here for the sake of brevity: The luciferase expression vector pGL-2 was supplied by Promega, and pGL-E vector derived from pGL-2 by an inframe insertion of a 54 bp Xba1 fragment encoding the 16 amino acid residue E region in a single Xba1 site in the luciferase coding region. To generate pGL-Eb, a PCR fragment was amplified using E5-X (5'GCTCTAGAGCCCAGTATAGA-3' (SEQ ID NO:14)) and E3-X (5'-GCTCTAGATGTCTCAAGCCTTTCCC-3' (SEQ ID NO:15)) as primers, pG4DP-3α (Ormondroyd et al., 1995) as the template and cloned into the single Xba1 site in pGL-2. pG4-DP-l has been already described (Bandara et al., 1993) and pRcCMV-HAE2F1 (Krek et al., 1994), expressing HA-tagged human E2F-1 was a gift of Dr W Krek. pCmV-DP-1/NLS was made by inserting a fragment containing the Bel 1 bi-partite NLS (amino acid residue 194 to 227) amplified by PCR into the Kpnl site (residue 327) of the DP-1 cDNA in pG4-DP-1. The nature of all the constructions were confirmed through sequence analysis.

The cells were grown in Dulbecco's modified Eagle's medium supplemented with 10% foetal calf serum (FCS). Cells were transfected by the liposome-mediated method, using the Lipofectin reagent (Gibco BRL) and according to manufacturer's recommendations. Sixty hours after transfection, cells were lysed in ice cold low salt buffer (LSB; 10 mM Tris-HCl pH 8, 7.5 mM $SO_4(NH_4)_2$, 1 mM EDTA, 0.025% NP-40) by using 0.2 ml of LSB per 6-cm-diameter dish. Lysates were incubated in ice for 5 min, and centrifuged at 3000 rpm for 3 min. The resulting pellets were resuspended in 0.2 ml of high salt buffer (HSB; 50 mM Tris-HCl pH 8, 150 mM NaCl, 5 mM EDTA, 0.5% NP-40) and centrifuged at 10,000 rpm for 5 min. Both buffers, LSB and HSB, were supplemented with protease inhibitors and 1 mM dithiothreitol. The insoluble material contained in the pellets of the last centrifugation were resuspended in 0.2 ml of SDS-sample buffer.

Usually, about 5% of the different fractions was used in immunoblotting. Samples were separated on a 10% SDS-polyacrylamide gel and transferred to nitrocellulose membranes. The membrane was blocked with 5% dried milk powder in PBS for 1 h, anti-DP-3 antibody (1:200, rabbit serum) was added and incubated for additional 1 h at room temperature. After three washes in PBS with 0.2% Tween-20, the blot was incubated with alkaline phosphatase-conjugated goat anti-rabbit IgG (1:7500, Promega) for 1 h at room temperature, washed three times in PBS-0.2% Tween 20 and developed. Anti serum 7.5, raised against a peptide containing DEEDEEEDPSSPE (SEQ ID NO:16) derived from DP-3, was used in the immunoblotting experiments.

The initial treatment with low salt (0.01 M) releases mostly soluble cytoplasmic proteins, the high salt (0.5 M) both nuclear and cytoplasmic, the insoluble material remaining being collected in fraction designated P. When cells expressing the β variant were treated according to this regime and the levels of β monitored by immunoblotting, it was found to be present throughout the fractions, being moderately enriched in the low salt fraction. In contrast, when cells expressing δ were treated in a similar fashion, the δ protein was far more enriched in the P fraction. Thus, the extraction properties of β and δ are different, and the E region (the only difference between β and δ proteins) is responsible for these differences.

It was possible that the differences in biochemical properties reflected distinct intracellular distributions of the DP-3 proteins. To test this idea we expressed each of the variants in COS7 cells and determined their intracellular location by immunostaining using anti-DP-3 7.2, an antiserum useful for this purpose since it only recognises the exogenous DP-3 protein. For the immunofluorescences, cells were grown on coverslips in 3 cm diameter dishes.

When either the α, β, γ or δ variant was expressed in COS7 cells, their intracellular distribution fell into two distinct categories: α and δ accumulated in nuclei whereas β and γ were distributed throughout the cytoplasm with a low level staining in nuclei. Although the α and δ proteins were exclusively nuclear, within a transfected culture of asynchronous cells minor variation was apparent in the distribution of β and γ proteins. For example, β and γ were usually present at higher levels in the cytoplasm relative to nuclei although occasional cells (less than 5% of transfected cells) were seen in which the proteins were present at similar levels in both the nucleus and the cytoplasm, a possible explanation for these observations being suggested later. In summary, these data establish that the differences in protein sequence between the variants influences their intracellular distribution. Specifically, the presence of the E regions in α and δ, but not β and γ, correlates with the ability of the protein to efficiently accumulate in nuclei.

The immunofluorescence was performed as follows. Transfected cells were fixed in 4% formaldehyde, rinsed and permeabilized in phosphate-buffered saline (PBS) containing 1% Triton X-100. Fixed cells were blocked in PBS containing 1% FCS, incubated with the primary antibodies diluted in PBS-1% FCS for 30 min at room temperature, washed three times with PBS and incubated with the secondary antibodies diluted in PBS-10% FCS for 30 min at room temperature. After a final wash with PBS, the coverslips were mounted on slides using Citofluor and examined with a Zeiss microscope. Magnification was 630x unless otherwise indicated.

As primary antibodies we used a rabbit polyclonal serum raised against a DP-3 specific peptide common to all the DP-3 variants called 7.2, a rabbit polyclonal serum which detects luciferase (Promega), a DP-1 antiserum (098) raised against a C-terminal peptide in DP-1 and the anti-HA monoclonal antibody 12CA5 (BabCO). Secondary antibodies were goat anti-rabbit IgG conjugated to fluorescein isothiocyanate (1:200, FITC) and goat anti-mouse IgG conjugated to tetramethylrhodamine isothiocyanate (1:200, TRITC) (Southern Biotechnology Associates Inc). Anti-peptide serum 7.2 was raised against the sequence VALATGQLPASNSHQ (SEQ ID NO:17) common to all DP-3 proteins.

EXAMPLE 6

The E region is necessary for nuclear localization

Since the only difference between the β and δ protein is the 16 amino acid residue E region, the E region must be necessary for the nuclear accumulation of δ. To test this idea, we removed the E region from the α variant (which like δ accumulates in nuclei) to create αΔE, and compared the intracellular distribution of the mutated protein to that of wild-type α by immunofluorescence in transfected COS7 cells as described above. The results indicated that in the absence of the E region the intracellular distribution of αΔE was altered to one which resembled the distribution of β since it failed to efficiently accumulate in nuclei. These data support the implications from the previous studies on a requirement for the E region in efficient nuclear accumulation, and thus suggest that it may function as or contribute to a nuclear localization signal (NLS).

EXAMPLE 7

An extended E region functions as a nuclear localization signal

An NLS can be experimentally defined by its deletion causing a loss of nuclear accumulation or by transferring the phenotype to a non nuclear protein. The previous results indicate that the properties of the E region are compatible with the first statement. To address the second, we attached the E region or an extended E region containing an additional 8 residues from the C-terminal boundary, onto luciferase (see Example 5 above for plasmid constructions).

When expressed in COS7 cells, wild-type luciferase was distributed throughout the cell, being marginally more abundant within the cytoplasm; the protein had a very similar distribution in all cells expressing wild-type luciferase. The insertion of the E region (pGL-E) did not significantly alter the distribution of the luciferase protein. However, when an additional 8 residues was inserted (pGL-Eb) nuclear accumulation became far more efficient. Thus, the E region together with additional residues located further on from the C-terminal boundary is necessary for efficient nuclear accumulation.

Together, these data suggest that the E region is necessary but not sufficient for the nuclear accumulation phenotype, and thus the 16 residue sequence is unlikely to contain an autonomous nuclear localization signal. Rather, the E region functions in a co-operative fashion with an additional part of the protein located at the C-terminal boundary of the E region to confer nuclear accumulation. In this respect, the insertion of the E region may produce a bi-partite nuclear localization signal characteristic of many eukaryotic nuclear proteins, such as nucleoplasmin (Dingwall and Laskey, 1991).

EXAMPLE 8

The E region is encoded by an alternatively spliced exon

Although it was very likely that the presence of the E region is regulated by alternative splicing, it was not clear whether a discrete exon encoded the 16 amino acid residues. To clarify this question we isolated the DP-3 gene and characterised its genomic organization across the region encoding the E sequence. For this, a genomic library prepared from murine embryonic stem cells was screened with the DP-3 cDNA, positive clones isolated and thereafter the relationship between genomic and cDNA sequence established.

A γGEM12 genomic library prepared from embryonic stem cell line SV129D3 was plated (approximately $10^6$ pfu) and transferred to Hybond N (Amersham International). Filters were hybridised in QuikHyb solution (Stratagene) at 65° C. with a $^{32}$P labelled mouse DP-3α cDNA (Ormondroyd et al, 1995). A positive genomic clone which contained the genomic E region was identified via southern blotting using a radiolabelled oligonucleotide antisense to the E region (358–407 bp DP-3α). A genomic fragment containing the E exon was then cloned into pEluescript (pBS, Stratagene) and sequenced using a Sequenase version 2.0 kit (UBS). Oligonucleotides for PCR and sequencing were made from E+mouse DP-3 cDNA sequences (Ormondroyd et al, 1995). Oligonucleotide sequences were as follows: 5' of E region, 7.16S; 5' CACCCGCAATGGTCACT-3' (SEQ ID NO:18), 3' of E region, 7.17A; 5'-ATGTCTCAAGCCTTTCCC-3' (SEQ ID NO:19), 5' end of E region E1-S; 5'-GATAGAAAACGAGCTAGAG-3' (SEQ ID NO:20), 3' end of E region, E2-A; 5'-TTCTGAGAAATCAGAGTCTA-3' (SEQ ID NO:21).

The analysis indicated that the 16 residues which constitute the E region are indeed encoded by a single 48 bp exon. Conventional splice acceptor and donor sites exist for the boundaries of the E exon which, in turn, lead into two large introns and, subsequently, exon sequence encoding the surrounding DP-3 protein. This isolation and characterisation of the DP-3 gene indicated that the E region is encoded by a discrete alternatively spliced exon.

EXAMPLE 9

DP-1 lacks an autonomous nuclear localization signal

A comparison of the E region of DP-3 with the same region of DP-1 indicated that DP-1 lacks a domain analogous to E (Ormondroyd et al, 1995). Furthermore, extensive searches to isolate alternatively spliced DP-1 mRNAs have so far failed and thus we investigated the intracellular location of exogenous DP-1 when expressed in COS7 cells, using methods essentially as described in Example 5.

The DP-1 protein had a similar distribution to the β and γ (E-minus) forms of DP-3, since it was located throughout the cytoplasm with occasional low level staining in nuclei, such a result being entirely compatible with the absence of the E region. The absence of DP-1 in nuclei was due to the lack of a NLS since the exogenous DP-1 could efficiently accumulate in nuclei after attaching a foreign nuclear localization signal (NLS), the bi-partite signal taken from the Bel 1 protein (Chang et al., 1995). These data suggest that DP-1 is not actively retained in the cytoplasm but rather its cytoplasmic location is passive.

EXAMPLE 10

E2F-1 can recruit DP-1 and cytoplasmic DP-3 proteins to nuclei

The result of Example 9 suggests that the cytoplasmic location of exogenous DP-1 is passive. We reasoned that in the absence of an autonomous NLS a possible mechanism to promote the nuclear accumulation of DP-1 may involve an interaction with its physiological partner, namely the E2F-1 protein. To test this idea, we studied the location of the E2F-1 protein in COS7 cells and thereafter the effect of co-expressing E2F-1 and DP-1 in the same cells.

An E2F-1 protein tagged with a haemagglutinin (HA) epitope and visualised by immunostaining with an anti-HA monoclonal antibody was exclusively nuclear. To assess the influence of E2F-1 on DP-1, both proteins were co-expressed and their intracellular distribution determined by double immunostaining with anti-HA monoclonal antibody and rabbit anti-DP-1. Neither the fluorescein-congugated anti-rabbit immunoglobulin or rhodamine-congugated anti-mouse immunoglobulin cross-reacted with the anti-HA monoclonal antibody or the rabbit anti-DP-1 respectively.

There was a striking difference in the distribution of DP-1 upon co-expression of E2F-1: cells expressing the E2F-1 protein contained nuclear DP-1, in contrast to its cytoplasmic location in the absence of E2F-1. In the rare exceptions where the transfected cells expressed only DP-1 (about 1% of total transfected population) the exogenous DP-1 was cytoplasmic. These data strongly suggest that upon forming a DP-1/E2F-1 heterodimer, E2F-1 has a dominant influence on recruiting DP-1 to a nuclear location.

We assessed if E2F-1 had a similar effect on DP-3β and αΔE. Co-expression of DP-3 β or αΔE with E2F-1 resulted in nuclear recruitment. The presence of DP-1 or DP-3β in nuclei is likely therefore to be dependent upon an interaction with the appropriate E2F heterodimeric partner which subsequently causes the efficient nuclear accumulation of DP proteins.

REFERENCES

Altmann, M. and Trachsel, H. (1993). *Trends Biochem. Sci.* 18, 429–432.

Bandara, L. R., Buck, V. M., Zamanian, M., Johnston, L. H. and La Thangue, N. B. (1993). *EMBO J.* 12, 4317–4324.

Bandara, L. R., Lam, E. W.-F., Sørensen, T. S., Zamanian, M., Girling, R. and La Thangue, N. B. (1994). *EMBO J.* 13, 3104–3114.

Beijersbergen, R. L., Kerkhoven, R. M., Zhu, L., Carlee, L., Voorhoeve, P. M. and Bernards, R. (1994). *Genes. Dev.* 8, 2680–2690.

Boulikas, T. (1994). *J. Cell Biochem.* 55: 32–38.

Boulikas, T. (1993). *Crit. Rev. Eukar. Gene Expr.* 3: 193–227.

Buck, V., Allen, E. K., Sørensen, T., Bybee, A., Hijmans, E. M., Voorhoeve, P. M., Bernards, R. and La Thangue, N. B. (1995). *Oncogene,* 11, 31–38.

Chang, J., Lee K. J., Jang, K. L., Lee, E. K., Baek, G. H. and Sung, Y. C. (1995). *J. Virology* 69: 801–808.

Cobrinik, D., Whyte, P., Peeper, D. S., Jacks, T. and Weinberg, R. A. (1993). *Genes Dev.*7, 2392–2404.

Descombes, P. and Schibler, U. (1991). *Cell* 67, 569–579.

Dingwall, C. and Laskey, R. (1991). *Trends. Biochem. Sci* 16: 478–481.

Dynlacht, B. D., Flores, O., Lees, J. A. and Harlow, E. (1994). *Genes Dev.* 8, 1772–1786.

Fields, S. and Song, O. (1989). *Nature* 340, 245–246.

Flemington, E. K., Speck, S. H. and Kaelin, W. G. (1993). *Proc. Natl. Acad. Sci. USA.* 90, 6914–6918.

Geballe, A. P. and Morris, D. R. (1994). *Trends Biochem. Sci.* 19, 159–164.

Ginsberg, D., Vairo, G., Chittenden, T., Xiao, Z. -X., Xu. G., Wydner, K. L., DeCaprio, J. A., Lawrence, J. B. and Livingston, D. M. (1994). *Genes. Dev.* 8, 2665–2679.

Girling, R., Partridge, J. F., Bandara, L. R., Burden, N., Totty, N. F., Hsuan, J. J. and La Thangue, N. B. (1993). *Nature* 362, 83–87.

Girling, R., Bandara, L. R., Ormondroyd, E., Lam, E. W. -F., Kotecha, S., Mohun, T. and La Thangue, N. B. (1994). *Mol. Biol. Cell.* 5, 1081–1092.

Heibert, S. W., Chellappan, S. P., Horowitz, J. M. and Nevins, J. R. (1992). *Genes Dev.* 6, 177–185.

Helin, K., Lees, J. A., Vidal, M., Dyson, N., Harlow, E. and Fattaey, A. (1992). *Cell* 70, 337–350.

Helin, K., Wu, C.-L., Fattaey, A. R., Lees, J. A., Dynlacht, B. D., Ngwu, C. and Harlow, E. (1993). *Genes Dev.* 7, 1850–1861.

Helin, K., Harlow, E. and Fattaey, A. R. (1993). *Mol. Cell. Biol.* 13: 6501–6508.

Hiebert, S. W., Chellappan, S. P., Horowitz, J. M. and Nevins, J. R. (1992). *Genes Dev.* 6: 177–185.

Hill, J. R. and Morris, D. R. (1993). *J. Biol. Chem.*268, 726–731.

Hill, C. S. and Treisman, R. (1995). *Cell* 80, 199–211.

Hinds, P. W., Mittnacht, S., Dulic, V., Arnold, A., Reed, S. L. and Ivey-Hoyle, M., Conroy, R., Huber, H. E., Goodhart, P. J., Oliff, A. and Heimbrook, D. C. (1993). *Mol. Cell. Biol.* 13, 7802–7812.

Kaelin, W. G., Krek, W., Sellers, W. R., DeCaprio, J. A., Ajchenbaum, F., Fuchs, C. S., Chittenden, T., Li, Y., Farnham, P. J., Blanar, M. A., Livingston, D. M. and Flemington, E. K. (1992). *Cell* 70, 351–364.

Kozak, M. (1987). *Nucleic Acid Res.* 15, 8125–8148.

Krek, W., Ewen, M. E., Shirodkar, S., Arany, Z., Kaelin, W. G. and Livingston, D. M. (1994). *Cell* 78, 161–172.

Krek, W., Livingston, D. M. and Shirodkar, S. (1993). *Science* 262, 1557–1560.

La Thangue, N., Thimmappaya, B. and Rigby, P. W. J. (1990). *Nucl. Acids. Res.* 18, 2929–2938.

La Thangue, N. B. (1994). *Trends Biochem. Sci.* 19, 108–114.

Lam, E. W. -F. and La Thangue, N. B. (1994). *Curr. Op. Cell Biol.* 6, 859–866.

Lees, J. A., Saito, M., Vidal, M., Valentine, M., Look, T., Harlow, E., Dyson, N. and Helin, K. (1993). *Mol. Cell. Biol.* 13, 7813–7825.

Lees, E., Faha, B., Dulic, V., Reed, S. I. and Harlow, E. (1992). *Genes Dev.* 6, 1874–1885.

Li, Y., Graham, C., Lacy, S., Duncan, D. M. V. and Whyte, P. (1993). *Genes Dev.* 7, 2366–2377.

Nevins, J. R. (1992). *Science* 258, 424–429.

Ormondroyd, E., de la Luna, S. and La Thangue, N. (1995) *Oncogene* 11, 1437–1446.

Schwarz, J. K., Devoto, S. H., Smith, E. J., Chellappan, S. P., Jakoi, L. and Nevins, J. R. (1993). *EMBO J.* 12, 1013–1020.

Shan, B., Zhu, X., Chen, P. L., Durfee, T., Yang, Y., Sharp, D. and Lee, W. H. (1992). *Mol. Cell. Biol.* 12, 5620–5631.

Shirodkar, S., Ewen, M., DeCaprio, J. A., Morgan, J., Livingston, D. M. and Chittenden, T. (1992). *Cell* 68, 157–166.

Smith, D. B. and Johnson, K. S. (1988). *Gene* 67, 31–37.

Thomas, B. J. and Rothestein, R. (1989). *Cell* 56, 619–630.

Treacy, M. N., Neilson, L. I., Turner, E. E., He, X. and Rosenfeld, M. G. (1992). *Cell* 68, 491–505.

Webster, N. J. G., Green, S., Tasset, D., Ponglikitmongkol, M. and Chambon, P. (1989). *EMBO. J.* 8: 1441–1446.

Weinberg, R. A. (1995). *Cell* 81: 323–330.

Wu, C. -L., Zukerberg, L. R., Ngwu, C., Harlow, E. and Lees, J. A. (1995). *Mol. Cell. Biol.* 15, 2536–2546.

Zamanian, M. and La Thangue, N. B. (1992). *EMBO J.* 11, 2603–2610.

Zamanian, M. and La Thangue, N. B. (1993). *Mol. Biol. Cell.* 4,389–396.

Zhang, Y. and Chellappan, S. (1995). *Oncogene,* 10, 2085–2093.

Zhu, L., Van der Heurel, S., Helin, K., Fattaey, A., Ewen, M., Livingston, D., Dyson, N. and Harlow, E. (1993). *Genes Dev.* 7, 1111–1125.

We claim:

1. An isolated polypeptide consisting of a sequence selected from the group consisting of SEQ ID NO:2, SEQ ID NO:4, SEQ ID NO:6, and SEQ ID NO:8.

2. An isolated polypeptide which comprises amino acids 1 to 61 of the sequence set forth as SEQ ID NO:2.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
  ( A ) LENGTH: 1385 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 1..1338

( x i ) SEQUENCE DESCRIPTION: SEQ ID NO:1:

```
ATG  ACG  GCA  AAA  AAT  GTT  GGT  TTG  CCA  TCC  ACA  AAT  GCA  GAG  CTG  AGG      48
Met  Thr  Ala  Lys  Asn  Val  Gly  Leu  Pro  Ser  Thr  Asn  Ala  Glu  Leu  Arg
 1              5                   10                  15

GGC  TTT  ATA  GAT  CAG  AAT  TTC  AGT  CCA  ACG  AAA  GGT  AAC  ATT  TCA  CTT      96
Gly  Phe  Ile  Asp  Gln  Asn  Phe  Ser  Pro  Thr  Lys  Gly  Asn  Ile  Ser  Leu
              20                   25                       30

GTT  GCC  TTT  CCA  GTT  TCA  AGC  ACC  AAC  TCA  CCA  ACA  AAG  ATT  TTA  CCG     144
Val  Ala  Phe  Pro  Val  Ser  Ser  Thr  Asn  Ser  Pro  Thr  Lys  Ile  Leu  Pro
         35                        40                       45

AAA  ACC  TTA  GGG  CCA  ATA  AAT  GTG  AAT  GTT  GGA  CCC  CAA  ATG  ATT  ATA     192
Lys  Thr  Leu  Gly  Pro  Ile  Asn  Val  Asn  Val  Gly  Pro  Gln  Met  Ile  Ile
     50                   55                       60

AGC  ACA  CCG  CAG  AGA  ATT  GCC  AAT  TCA  GGA  AGT  GTT  CTG  ATT  GGG  AAT     240
Ser  Thr  Pro  Gln  Arg  Ile  Ala  Asn  Ser  Gly  Ser  Val  Leu  Ile  Gly  Asn
 65                       70                       75                       80

CCA  TAT  ACC  CCT  GCA  CCC  GCA  ATG  GTC  ACT  CAG  ACT  CAC  ATA  GCT  GAG     288
Pro  Tyr  Thr  Pro  Ala  Pro  Ala  Met  Val  Thr  Gln  Thr  His  Ile  Ala  Glu
                   85                        90                       95

GCT  GCT  GGC  TGG  GTT  CCC  AGT  GAT  AGA  AAA  CGA  GCT  AGA  GAA  TTT  ATA     336
Ala  Ala  Gly  Trp  Val  Pro  Ser  Asp  Arg  Lys  Arg  Ala  Arg  Glu  Phe  Ile
              100                      105                      110

GAC  TCT  GAT  TTT  TCA  GAA  AGT  AAA  CGA  AGC  AAA  AAA  GGA  GAT  AAA  AAT     384
Asp  Ser  Asp  Phe  Ser  Glu  Ser  Lys  Arg  Ser  Lys  Lys  Gly  Asp  Lys  Asn
         115                      120                      125

GGG  AAA  GGC  TTG  AGA  CAT  TTT  TCA  ATG  AAG  GTG  TGT  GAG  AAA  GTT  CAG     432
Gly  Lys  Gly  Leu  Arg  His  Phe  Ser  Met  Lys  Val  Cys  Glu  Lys  Val  Gln
     130                      135                      140

CGG  AAA  GGC  ACA  ACT  TCA  TAC  AAT  GAG  GTA  GCT  GAT  GAG  CTG  GTA  TCT     480
Arg  Lys  Gly  Thr  Thr  Ser  Tyr  Asn  Glu  Val  Ala  Asp  Glu  Leu  Val  Ser
145                       150                      155                      160

GAG  TTT  ACC  AAC  TCA  AAT  AAC  CAT  CTG  GCA  GCT  GAT  TCG  GCT  TAT  GAT     528
Glu  Phe  Thr  Asn  Ser  Asn  Asn  His  Leu  Ala  Ala  Asp  Ser  Ala  Tyr  Asp
                   165                      170                      175

CAG  GAG  AAC  ATT  AGA  CGA  AGA  GTT  TAT  GAT  GCT  TTA  AAT  GTA  CTA  ATG     576
Gln  Glu  Asn  Ile  Arg  Arg  Arg  Val  Tyr  Asp  Ala  Leu  Asn  Val  Leu  Met
              180                      185                      190

GCG  ATG  AAC  ATA  ATT  TCA  AAG  GAA  AAA  AAA  GAA  ATC  AAG  TGG  ATT  GGC     624
Ala  Met  Asn  Ile  Ile  Ser  Lys  Glu  Lys  Lys  Glu  Ile  Lys  Trp  Ile  Gly
         195                      200                      205

CTG  CCT  ACC  AAT  TCT  GCT  CAG  GAA  TGC  CAG  AAC  CTG  GAA  ATC  GAG  AAG     672
Leu  Pro  Thr  Asn  Ser  Ala  Gln  Glu  Cys  Gln  Asn  Leu  Glu  Ile  Glu  Lys
     210                      215                      220
```

| | | | | | | | | | | | | | | | |
|---|---|---|---|---|---|---|---|---|---|---|---|---|---|---|---|
| CAG | AGG | CGG | ATA | GAA | CGG | ATA | AAG | CAG | AAG | CGA | GCC | CAG | CTA | CAA | GAA | 720 |
| Gln | Arg | Arg | Ile | Glu | Arg | Ile | Lys | Gln | Lys | Arg | Ala | Gln | Leu | Gln | Glu |
| 225 | | | | 230 | | | | 235 | | | | | | 240 |
| CTT | CTC | CTT | CAG | CAA | ATT | GCT | TTT | AAA | AAC | CTG | GTA | CAG | AGA | AAT | CGA | 768 |
| Leu | Leu | Leu | Gln | Gln | Ile | Ala | Phe | Lys | Asn | Leu | Val | Gln | Arg | Asn | Arg |
| | | | | 245 | | | | 250 | | | | | 255 |
| CAA | AAT | GAA | CAA | CAA | AAC | CAG | GGC | CCT | CCA | GCT | GTG | AAT | TCC | ACC | ATT | 816 |
| Gln | Asn | Glu | Gln | Gln | Asn | Gln | Gly | Pro | Pro | Ala | Val | Asn | Ser | Thr | Ile |
| | | | 260 | | | | 265 | | | | | 270 |
| CAG | CTG | CCA | TTT | ATA | ATC | ATT | AAT | ACA | AGC | AGG | AAA | ACA | GTC | ATA | GAC | 864 |
| Gln | Leu | Pro | Phe | Ile | Ile | Ile | Asn | Thr | Ser | Arg | Lys | Thr | Val | Ile | Asp |
| | | 275 | | | | 280 | | | | 285 |
| TGC | AGC | ATC | TCC | AGT | GAC | AAA | TTT | GAA | TAC | CTT | TTT | AAT | TTT | GAT | AAC | 912 |
| Cys | Ser | Ile | Ser | Ser | Asp | Lys | Phe | Glu | Tyr | Leu | Phe | Asn | Phe | Asp | Asn |
| | 290 | | | | 295 | | | | 300 |
| ACC | TTT | GAG | ATC | CAC | GAC | GAC | ATA | GAG | GTA | CTG | AAG | CGG | ATG | GGA | ATG | 960 |
| Thr | Phe | Glu | Ile | His | Asp | Asp | Ile | Glu | Val | Leu | Lys | Arg | Met | Gly | Met |
| 305 | | | | 310 | | | | 315 | | | | 320 |
| TCC | TTT | GGT | CTG | GAG | TCA | GGC | AAA | TGC | TCT | CTG | GAG | GAT | CTG | AAA | ATC | 1008 |
| Ser | Phe | Gly | Leu | Glu | Ser | Gly | Lys | Cys | Ser | Leu | Glu | Asp | Leu | Lys | Ile |
| | | | | 325 | | | | 330 | | | | 335 |
| GCA | AGA | TCC | CTG | GTT | CCA | AAA | GCT | TTA | GAA | GGC | TAT | ATT | ACA | GAT | ATC | 1056 |
| Ala | Arg | Ser | Leu | Val | Pro | Lys | Ala | Leu | Glu | Gly | Tyr | Ile | Thr | Asp | Ile |
| | | | 340 | | | | 345 | | | | | 350 |
| TCC | ACA | GGA | CCT | TCT | TGG | TTA | AAT | CAG | GGA | CTA | CTT | TTG | AAC | TCT | ACC | 1104 |
| Ser | Thr | Gly | Pro | Ser | Trp | Leu | Asn | Gln | Gly | Leu | Leu | Leu | Asn | Ser | Thr |
| | | 355 | | | | 360 | | | | 365 |
| CAA | TCA | GTT | TCA | AAT | TTA | GAC | CCG | ACC | ACC | GGT | GCC | ACT | GTA | CCC | CAA | 1152 |
| Gln | Ser | Val | Ser | Asn | Leu | Asp | Pro | Thr | Thr | Gly | Ala | Thr | Val | Pro | Gln |
| | 370 | | | | 375 | | | | 380 |
| TCA | AGT | GTA | AAC | CAA | GGG | TTG | TGC | TTG | GAT | GCT | GAA | GTG | GCC | TTA | GCA | 1200 |
| Ser | Ser | Val | Asn | Gln | Gly | Leu | Cys | Leu | Asp | Ala | Glu | Val | Ala | Leu | Ala |
| 385 | | | | 390 | | | | 395 | | | | 400 |
| ACT | GGG | CAG | CTC | CCT | GCC | TCA | AAC | AGT | CAC | CAG | TCC | AGC | AGT | GCA | GCC | 1248 |
| Thr | Gly | Gln | Leu | Pro | Ala | Ser | Asn | Ser | His | Gln | Ser | Ser | Ser | Ala | Ala |
| | | | 405 | | | | 410 | | | | 415 |
| TCT | CAC | TTC | TCG | GAG | TCC | CGC | GGC | GAG | ACC | CCC | TGT | TCA | TTC | AAC | GAT | 1296 |
| Ser | His | Phe | Ser | Glu | Ser | Arg | Gly | Glu | Thr | Pro | Cys | Ser | Phe | Asn | Asp |
| | | | 420 | | | | 425 | | | | 430 |
| GAA | GAT | GAG | GAA | GAT | GAA | GAG | GAG | GAT | CCC | TCC | TCC | CCA | GAA | | | 1338 |
| Glu | Asp | Glu | Glu | Asp | Glu | Glu | Glu | Asp | Pro | Ser | Ser | Pro | Glu |
| | | 435 | | | | 440 | | | | 445 |

TAAAGACAGG AGAGAACTCA TGTTTTAAAA AAAAAAAAAA ACTCGAG 1385

( 2 ) INFORMATION FOR SEQ ID NO:2:

( i ) SEQUENCE CHARACTERISTICS:
        ( A ) LENGTH: 446 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Thr | Ala | Lys | Asn | Val | Gly | Leu | Pro | Ser | Thr | Asn | Ala | Glu | Leu | Arg |
|---|---|---|---|---|---|---|---|---|---|---|---|---|---|---|---|
| 1 | | | | 5 | | | | | 10 | | | | | 15 |

| Gly | Phe | Ile | Asp | Gln | Asn | Phe | Ser | Pro | Thr | Lys | Gly | Asn | Ile | Ser | Leu |
|---|---|---|---|---|---|---|---|---|---|---|---|---|---|---|---|
| | | | 20 | | | | | 25 | | | | | 30 |

| Val | Ala | Phe | Pro | Val | Ser | Ser | Thr | Asn | Ser | Pro | Thr | Lys | Ile | Leu | Pro |
|---|---|---|---|---|---|---|---|---|---|---|---|---|---|---|---|
| | | | 35 | | | | | 40 | | | | | 45 |

| Lys | Thr | Leu | Gly | Pro | Ile | Asn | Val | Asn | Val | Gly | Pro | Gln | Met | Ile | Ile |
|---|---|---|---|---|---|---|---|---|---|---|---|---|---|---|---|

|     |     |     |     |     | 50  |     |     |     |     | 55  |     |     |     |     | 60  |
| --- | --- | --- | --- | --- | --- | --- | --- | --- | --- | --- | --- | --- | --- | --- | --- |
| Ser | Thr | Pro | Gln | Arg | Ile | Ala | Asn | Ser | Gly | Ser | Val | Leu | Ile | Gly | Asn |
| 65  |     |     |     |     | 70  |     |     |     |     | 75  |     |     |     |     | 80  |
| Pro | Tyr | Thr | Pro | Ala | Pro | Ala | Met | Val | Thr | Gln | Thr | His | Ile | Ala | Glu |
|     |     |     |     | 85  |     |     |     |     | 90  |     |     |     |     | 95  |     |
| Ala | Ala | Gly | Trp | Val | Pro | Ser | Asp | Arg | Lys | Ala | Arg | Glu | Phe | Ile |     |
|     |     |     |     | 100 |     |     |     |     | 105 |     |     |     |     | 110 |     |
| Asp | Ser | Asp | Phe | Ser | Glu | Ser | Lys | Arg | Ser | Lys | Lys | Gly | Asp | Lys | Asn |
|     |     |     | 115 |     |     |     |     | 120 |     |     |     |     | 125 |     |     |
| Gly | Lys | Gly | Leu | Arg | His | Phe | Ser | Met | Lys | Val | Cys | Glu | Lys | Val | Gln |
|     |     | 130 |     |     |     | 135 |     |     |     |     | 140 |     |     |     |     |
| Arg | Lys | Gly | Thr | Thr | Ser | Tyr | Asn | Glu | Val | Ala | Asp | Glu | Leu | Val | Ser |
| 145 |     |     |     |     | 150 |     |     |     |     | 155 |     |     |     |     | 160 |
| Glu | Phe | Thr | Asn | Ser | Asn | Asn | His | Leu | Ala | Ala | Asp | Ser | Ala | Tyr | Asp |
|     |     |     |     | 165 |     |     |     |     | 170 |     |     |     |     | 175 |     |
| Gln | Glu | Asn | Ile | Arg | Arg | Arg | Val | Tyr | Asp | Ala | Leu | Asn | Val | Leu | Met |
|     |     |     | 180 |     |     |     |     | 185 |     |     |     |     | 190 |     |     |
| Ala | Met | Asn | Ile | Ile | Ser | Lys | Glu | Lys | Lys | Glu | Ile | Lys | Trp | Ile | Gly |
|     |     | 195 |     |     |     |     | 200 |     |     |     |     | 205 |     |     |     |
| Leu | Pro | Thr | Asn | Ser | Ala | Gln | Glu | Cys | Gln | Asn | Leu | Glu | Ile | Glu | Lys |
|     | 210 |     |     |     |     | 215 |     |     |     |     | 220 |     |     |     |     |
| Gln | Arg | Arg | Ile | Glu | Arg | Ile | Lys | Gln | Lys | Arg | Ala | Gln | Leu | Gln | Glu |
| 225 |     |     |     |     | 230 |     |     |     |     | 235 |     |     |     |     | 240 |
| Leu | Leu | Leu | Gln | Gln | Ile | Ala | Phe | Lys | Asn | Leu | Val | Gln | Arg | Asn | Arg |
|     |     |     |     | 245 |     |     |     |     | 250 |     |     |     |     | 255 |     |
| Gln | Asn | Glu | Gln | Gln | Asn | Gln | Gly | Pro | Pro | Ala | Val | Asn | Ser | Thr | Ile |
|     |     |     | 260 |     |     |     |     | 265 |     |     |     |     | 270 |     |     |
| Gln | Leu | Pro | Phe | Ile | Ile | Ile | Asn | Thr | Ser | Arg | Lys | Thr | Val | Ile | Asp |
|     |     | 275 |     |     |     |     | 280 |     |     |     |     | 285 |     |     |     |
| Cys | Ser | Ile | Ser | Ser | Asp | Lys | Phe | Glu | Tyr | Leu | Phe | Asn | Phe | Asp | Asn |
|     | 290 |     |     |     |     | 295 |     |     |     |     | 300 |     |     |     |     |
| Thr | Phe | Glu | Ile | His | Asp | Asp | Ile | Glu | Val | Leu | Lys | Arg | Met | Gly | Met |
| 305 |     |     |     |     | 310 |     |     |     |     | 315 |     |     |     |     | 320 |
| Ser | Phe | Gly | Leu | Glu | Ser | Gly | Lys | Cys | Ser | Leu | Glu | Asp | Leu | Lys | Ile |
|     |     |     |     | 325 |     |     |     |     | 330 |     |     |     |     | 335 |     |
| Ala | Arg | Ser | Leu | Val | Pro | Lys | Ala | Leu | Glu | Gly | Tyr | Ile | Thr | Asp | Ile |
|     |     |     | 340 |     |     |     |     | 345 |     |     |     |     | 350 |     |     |
| Ser | Thr | Gly | Pro | Ser | Trp | Leu | Asn | Gln | Gly | Leu | Leu | Leu | Asn | Ser | Thr |
|     |     | 355 |     |     |     |     | 360 |     |     |     |     | 365 |     |     |     |
| Gln | Ser | Val | Ser | Asn | Leu | Asp | Pro | Thr | Thr | Gly | Ala | Thr | Val | Pro | Gln |
|     | 370 |     |     |     |     | 375 |     |     |     |     | 380 |     |     |     |     |
| Ser | Ser | Val | Asn | Gln | Gly | Leu | Cys | Leu | Asp | Ala | Glu | Val | Ala | Leu | Ala |
| 385 |     |     |     |     | 390 |     |     |     |     | 395 |     |     |     |     | 400 |
| Thr | Gly | Gln | Leu | Pro | Ala | Ser | Asn | Ser | His | Gln | Ser | Ser | Ser | Ala | Ala |
|     |     |     |     | 405 |     |     |     |     | 410 |     |     |     |     | 415 |     |
| Ser | His | Phe | Ser | Glu | Ser | Arg | Gly | Glu | Thr | Pro | Cys | Ser | Phe | Asn | Asp |
|     |     |     | 420 |     |     |     |     | 425 |     |     |     |     | 430 |     |     |
| Glu | Asp | Glu | Glu | Asp | Glu | Glu | Glu | Asp | Pro | Ser | Ser | Pro | Glu |     |     |
|     |     |     | 435 |     |     |     |     | 440 |     |     |     |     | 445 |     |     |

( 2 ) INFORMATION FOR SEQ ID NO:3:

( i ) SEQUENCE CHARACTERISTICS:
  ( A ) LENGTH: 1154 base pairs
  ( B ) TYPE: nucleic acid ( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..1107

( x i ) SEQUENCE DESCRIPTION: SEQ ID NO:3:

```
ATG ATT ATA AGC ACA CCG CAG AGA ATT GCC AAT TCA GGA AGT GTT CTG      48
Met Ile Ile Ser Thr Pro Gln Arg Ile Ala Asn Ser Gly Ser Val Leu
 1               5                  10                  15

ATT GGG AAT CCA TAT ACC CCT GCA CCC GCA ATG GTC ACT CAG ACT CAC      96
Ile Gly Asn Pro Tyr Thr Pro Ala Pro Ala Met Val Thr Gln Thr His
             20                  25                  30

ATA GCT GAG GCT GCT GGC TGG GTT CCC AGT AAA CGA AGC AAA AAA GGA     144
Ile Ala Glu Ala Ala Gly Trp Val Pro Ser Lys Arg Ser Lys Lys Gly
         35                  40                  45

GAT AAA AAT GGG AAA GGC TTG AGA CAT TTT TCA ATG AAG GTG TGT GAG     192
Asp Lys Asn Gly Lys Gly Leu Arg His Phe Ser Met Lys Val Cys Glu
     50                  55                  60

AAA GTT CAG CGG AAA GGC ACA ACT TCA TAC AAT GAG GTA GCT GAT GAG     240
Lys Val Gln Arg Lys Gly Thr Thr Ser Tyr Asn Glu Val Ala Asp Glu
 65                  70                  75                  80

CTG GTA TCT GAG TTT ACC AAC TCA AAT AAC CAT CTG GCA GCT GAT TCG     288
Leu Val Ser Glu Phe Thr Asn Ser Asn Asn His Leu Ala Ala Asp Ser
                 85                  90                  95

GCT TAT GAT CAG GAG AAC ATT AGA CGA AGA GTT TAT GAT GCT TTA AAT     336
Ala Tyr Asp Gln Glu Asn Ile Arg Arg Arg Val Tyr Asp Ala Leu Asn
             100                 105                 110

GTA CTA ATG GCG ATG AAC ATA ATT TCA AAG GAA AAA AAA GAA ATC AAG     384
Val Leu Met Ala Met Asn Ile Ile Ser Lys Glu Lys Lys Glu Ile Lys
         115                 120                 125

TGG ATT GGC CTG CCT ACC AAT TCT GCT CAG GAA TGC CAG AAC CTG GAA     432
Trp Ile Gly Leu Pro Thr Asn Ser Ala Gln Glu Cys Gln Asn Leu Glu
     130                 135                 140

ATC GAG AAG CAG AGG CGG ATA GAA CGG ATA AAG CAG AAG CGA GCC CAG     480
Ile Glu Lys Gln Arg Arg Ile Glu Arg Ile Lys Gln Lys Arg Ala Gln
145                 150                 155                 160

CTA CAA GAA CTT CTC CTT CAG CAA ATT GCT TTT AAA AAC CTG GTA CAG     528
Leu Gln Glu Leu Leu Leu Gln Gln Ile Ala Phe Lys Asn Leu Val Gln
                 165                 170                 175

AGA AAT CGA CAA AAT GAA CAA CAA AAC CAG GGC CCT CCA GCT GTG AAT     576
Arg Asn Arg Gln Asn Glu Gln Gln Asn Gln Gly Pro Pro Ala Val Asn
             180                 185                 190

TCC ACC ATT CAG CTG CCA TTT ATA ATC ATT AAT ACA AGC AGG AAA ACA     624
Ser Thr Ile Gln Leu Pro Phe Ile Ile Ile Asn Thr Ser Arg Lys Thr
         195                 200                 205

GTC ATA GAC TGC AGC ATC TCC AGT GAC AAA TTT GAA TAC CTT TTT AAT     672
Val Ile Asp Cys Ser Ile Ser Ser Asp Lys Phe Glu Tyr Leu Phe Asn
     210                 215                 220

TTT GAT AAC ACC TTT GAG ATC CAC GAC GAC ATA GAG GTA CTG AAG CGG     720
Phe Asp Asn Thr Phe Glu Ile His Asp Asp Ile Glu Val Leu Lys Arg
225                 230                 235                 240

ATG GGA ATG TCC TTT GGT CTG GAG TCA GGC AAA TGC TCT CTG GAG GAT     768
Met Gly Met Ser Phe Gly Leu Glu Ser Gly Lys Cys Ser Leu Glu Asp
                 245                 250                 255

CTG AAA ATC GCA AGA TCC CTG GTT CCA AAA GCT TTA GAA GGC TAT ATT     816
Leu Lys Ile Ala Arg Ser Leu Val Pro Lys Ala Leu Glu Gly Tyr Ile
             260                 265                 270

ACA GAT ATC TCC ACA GGA CCT TCT TGG TTA AAT CAG GGA CTA CTT TTG     864
```

```
Thr  Asp  Ile  Ser  Thr  Gly  Pro  Ser  Trp  Leu  Asn  Gln  Gly  Leu  Leu  Leu
          275                 280                      285

AAC  TCT  ACC  CAA  TCA  GTT  TCA  AAT  TTA  GAC  CCG  ACC  ACC  GGT  GCC  ACT         912
Asn  Ser  Thr  Gln  Ser  Val  Ser  Asn  Leu  Asp  Pro  Thr  Thr  Gly  Ala  Thr
     290                 295                      300

GTA  CCC  CAA  TCA  AGT  GTA  AAC  CAA  GGG  TTG  TGC  TTG  GAT  GCT  GAA  GTG         960
Val  Pro  Gln  Ser  Ser  Val  Asn  Gln  Gly  Leu  Cys  Leu  Asp  Ala  Glu  Val
305                      310                 315                           320

GCC  TTA  GCA  ACT  GGG  CAG  CTC  CCT  GCC  TCA  AAC  AGT  CAC  CAG  TCC  AGC        1008
Ala  Leu  Ala  Thr  Gly  Gln  Leu  Pro  Ala  Ser  Asn  Ser  His  Gln  Ser  Ser
               325                      330                      335

AGT  GCA  GCC  TCT  CAC  TTC  TCG  GAG  TCC  CGC  GGC  GAG  ACC  CCC  TGT  TCA        1056
Ser  Ala  Ala  Ser  His  Phe  Ser  Glu  Ser  Arg  Gly  Glu  Thr  Pro  Cys  Ser
               340                      345                 350

TTC  AAC  GAT  GAA  GAT  GAG  GAA  GAT  GAA  GAG  GAG  GAT  CCC  TCC  TCC  CCA        1104
Phe  Asn  Asp  Glu  Asp  Glu  Glu  Asp  Glu  Glu  Glu  Asp  Pro  Ser  Ser  Pro
               355                      360                 365

GAA  TAAAGACAGG  AGAGAACTCA  TGTTTTAAAA  AAAAAAAAAA  ACTCGAG                           1154
Glu
```

( 2 ) INFORMATION FOR SEQ ID NO:4:

( i ) SEQUENCE CHARACTERISTICS:
        ( A ) LENGTH: 369 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ile  Ile  Ser  Thr  Pro  Gln  Arg  Ile  Ala  Asn  Ser  Gly  Ser  Val  Leu
 1                  5                        10                      15

Ile  Gly  Asn  Pro  Tyr  Thr  Pro  Ala  Pro  Ala  Met  Val  Thr  Gln  Thr  His
               20                  25                      30

Ile  Ala  Glu  Ala  Ala  Gly  Trp  Val  Pro  Ser  Lys  Arg  Ser  Lys  Lys  Gly
          35                  40                      45

Asp  Lys  Asn  Gly  Lys  Gly  Leu  Arg  His  Phe  Ser  Met  Lys  Val  Cys  Glu
     50                  55                      60

Lys  Val  Gln  Arg  Lys  Gly  Thr  Thr  Ser  Tyr  Asn  Glu  Val  Ala  Asp  Glu
65                       70                      75                           80

Leu  Val  Ser  Glu  Phe  Thr  Asn  Ser  Asn  Asn  His  Leu  Ala  Ala  Asp  Ser
               85                       90                           95

Ala  Tyr  Asp  Gln  Glu  Asn  Ile  Arg  Arg  Arg  Val  Tyr  Asp  Ala  Leu  Asn
               100                     105                     110

Val  Leu  Met  Ala  Met  Asn  Ile  Ile  Ser  Lys  Glu  Lys  Lys  Glu  Ile  Lys
          115                     120                     125

Trp  Ile  Gly  Leu  Pro  Thr  Asn  Ser  Ala  Gln  Glu  Cys  Gln  Asn  Leu  Glu
     130                     135                     140

Ile  Glu  Lys  Gln  Arg  Arg  Ile  Glu  Arg  Ile  Lys  Gln  Lys  Arg  Ala  Gln
145                      150                     155                          160

Leu  Gln  Glu  Leu  Leu  Leu  Gln  Gln  Ile  Ala  Phe  Lys  Asn  Leu  Val  Gln
               165                     170                     175

Arg  Asn  Arg  Gln  Asn  Glu  Gln  Gln  Asn  Gln  Gly  Pro  Pro  Ala  Val  Asn
               180                     185                     190

Ser  Thr  Ile  Gln  Leu  Pro  Phe  Ile  Ile  Ile  Asn  Thr  Ser  Arg  Lys  Thr
          195                     200                     205

Val  Ile  Asp  Cys  Ser  Ile  Ser  Ser  Asp  Lys  Phe  Glu  Tyr  Leu  Phe  Asn
          210                     215                     220
```

| | | | | | | | | | | | | | | |
|---|---|---|---|---|---|---|---|---|---|---|---|---|---|---|
| Phe | Asp | Asn | Thr | Phe | Glu | Ile | His | Asp | Asp | Ile | Glu | Val | Leu | Lys | Arg |
| 225 | | | | | 230 | | | | 235 | | | | | 240 |
| Met | Gly | Met | Ser | Phe | Gly | Leu | Glu | Ser | Gly | Lys | Cys | Ser | Leu | Glu | Asp |
| | | | | 245 | | | | | 250 | | | | 255 | | |
| Leu | Lys | Ile | Ala | Arg | Ser | Leu | Val | Pro | Lys | Ala | Leu | Glu | Gly | Tyr | Ile |
| | | | 260 | | | | | 265 | | | | | 270 | | |
| Thr | Asp | Ile | Ser | Thr | Gly | Pro | Ser | Trp | Leu | Asn | Gln | Gly | Leu | Leu | Leu |
| | | 275 | | | | | 280 | | | | | 285 | | | |
| Asn | Ser | Thr | Gln | Ser | Val | Ser | Asn | Leu | Asp | Pro | Thr | Thr | Gly | Ala | Thr |
| | 290 | | | | | 295 | | | | | 300 | | | | |
| Val | Pro | Gln | Ser | Ser | Val | Asn | Gln | Gly | Leu | Cys | Leu | Asp | Ala | Glu | Val |
| 305 | | | | | 310 | | | | | 315 | | | | | 320 |
| Ala | Leu | Ala | Thr | Gly | Gln | Leu | Pro | Ala | Ser | Asn | Ser | His | Gln | Ser | Ser |
| | | | | 325 | | | | | 330 | | | | | 335 | |
| Ser | Ala | Ala | Ser | His | Phe | Ser | Glu | Ser | Arg | Gly | Glu | Thr | Pro | Cys | Ser |
| | | | 340 | | | | | 345 | | | | | 350 | | |
| Phe | Asn | Asp | Glu | Asp | Glu | Glu | Asp | Glu | Glu | Glu | Asp | Pro | Ser | Ser | Pro |
| | | 355 | | | | | 360 | | | | | 365 | | | |
| Glu | | | | | | | | | | | | | | | |

( 2 ) INFORMATION FOR SEQ ID NO:5:

( i ) SEQUENCE CHARACTERISTICS:
        ( A ) LENGTH: 1157 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1110

( x i ) SEQUENCE DESCRIPTION: SEQ ID NO:5:

| | | | | | | | | | | | | | | | |
|---|---|---|---|---|---|---|---|---|---|---|---|---|---|---|---|
| ATG | ATT | ATA | AGC | ACA | CCG | CAG | AGA | ATT | GCC | AAT | TCA | GGA | AGT | GTT | CTG | 48 |
| Met | Ile | Ile | Ser | Thr | Pro | Gln | Arg | Ile | Ala | Asn | Ser | Gly | Ser | Val | Leu | |
| 1 | | | | 5 | | | | | 10 | | | | | 15 | | |
| ATT | GGG | AAT | CCA | TAT | ACC | CCT | GCA | CCC | GCA | ATG | GTC | ACT | CAG | ACT | CAC | 96 |
| Ile | Gly | Asn | Pro | Tyr | Thr | Pro | Ala | Pro | Ala | Met | Val | Thr | Gln | Thr | His | |
| | | | 20 | | | | | 25 | | | | | 30 | | | |
| ATA | GCT | GAG | GCT | GCT | GGC | TGG | GTT | CCC | AGT | AAA | CGA | AGC | AAA | AAA | GGA | 144 |
| Ile | Ala | Glu | Ala | Ala | Gly | Trp | Val | Pro | Ser | Lys | Arg | Ser | Lys | Lys | Gly | |
| | | | 35 | | | | | 40 | | | | | 45 | | | |
| GAT | AAA | AAT | GGG | AAA | GGC | TTG | AGA | CAT | TTT | TCA | ATG | AAG | GTG | TGT | GAG | 192 |
| Asp | Lys | Asn | Gly | Lys | Gly | Leu | Arg | His | Phe | Ser | Met | Lys | Val | Cys | Glu | |
| | 50 | | | | | 55 | | | | | 60 | | | | | |
| AAA | GTT | CAG | CGG | AAA | GGC | ACA | ACT | TCA | TAC | AAT | GAG | GTA | GCT | GAT | GAG | 240 |
| Lys | Val | Gln | Arg | Lys | Gly | Thr | Thr | Ser | Tyr | Asn | Glu | Val | Ala | Asp | Glu | |
| 65 | | | | | 70 | | | | | 75 | | | | | 80 | |
| CTG | GTA | TCT | GAG | TTT | ACC | AAC | TCA | AAT | AAC | CAT | CTG | GCA | GCT | GAT | TCG | 288 |
| Leu | Val | Ser | Glu | Phe | Thr | Asn | Ser | Asn | Asn | His | Leu | Ala | Ala | Asp | Ser | |
| | | | | 85 | | | | | 90 | | | | | 95 | | |
| CAG | GCT | TAT | GAT | CAG | GAG | AAC | ATT | AGA | CGA | AGA | GTT | TAT | GAT | GCT | TTA | 336 |
| Gln | Ala | Tyr | Asp | Gln | Glu | Asn | Ile | Arg | Arg | Arg | Val | Tyr | Asp | Ala | Leu | |
| | | | 100 | | | | | 105 | | | | | 110 | | | |
| AAT | GTA | CTA | ATG | GCG | ATG | AAC | ATA | ATT | TCA | AAG | GAA | AAA | AAA | GAA | ATC | 384 |
| Asn | Val | Leu | Met | Ala | Met | Asn | Ile | Ile | Ser | Lys | Glu | Lys | Lys | Glu | Ile | |
| | | | 115 | | | | | 120 | | | | | 125 | | | |
| AAG | TGG | ATT | GGC | CTG | CCT | ACC | AAT | TCT | GCT | CAG | GAA | TGC | CAG | AAC | CTG | 432 |
| Lys | Trp | Ile | Gly | Leu | Pro | Thr | Asn | Ser | Ala | Gln | Glu | Cys | Gln | Asn | Leu | |

```
                   130                           135                          140
GAA  ATC  GAG  AAG  CAG  AGG  CGG  ATA  GAA  CGG  ATA  AAG  CAG  AAG  CGA  GCC          480
Glu  Ile  Glu  Lys  Gln  Arg  Arg  Ile  Glu  Arg  Ile  Lys  Gln  Lys  Arg  Ala
145                      150                      155                      160

CAG  CTA  CAA  GAA  CTT  CTC  CTT  CAG  CAA  ATT  GCT  TTT  AAA  AAC  CTG  GTA          528
Gln  Leu  Gln  Glu  Leu  Leu  Leu  Gln  Gln  Ile  Ala  Phe  Lys  Asn  Leu  Val
                         165                      170                      175

CAG  AGA  AAT  CGA  CAA  AAT  GAA  CAA  CAA  AAC  CAG  GGC  CCT  CCA  GCT  GTG          576
Gln  Arg  Asn  Arg  Gln  Asn  Glu  Gln  Gln  Asn  Gln  Gly  Pro  Pro  Ala  Val
               180                      185                            190

AAT  TCC  ACC  ATT  CAG  CTG  CCA  TTT  ATA  ATC  ATT  AAT  ACA  AGC  AGG  AAA          624
Asn  Ser  Thr  Ile  Gln  Leu  Pro  Phe  Ile  Ile  Ile  Asn  Thr  Ser  Arg  Lys
          195                      200                      205

ACA  GTC  ATA  GAC  TGC  AGC  ATC  TCC  AGT  GAC  AAA  TTT  GAA  TAC  CTT  TTT          672
Thr  Val  Ile  Asp  Cys  Ser  Ile  Ser  Ser  Asp  Lys  Phe  Glu  Tyr  Leu  Phe
          210                      215                      220

AAT  TTT  GAT  AAC  ACC  TTT  GAG  ATC  CAC  GAC  GAC  ATA  GAG  GTA  CTG  AAG          720
Asn  Phe  Asp  Asn  Thr  Phe  Glu  Ile  His  Asp  Asp  Ile  Glu  Val  Leu  Lys
225                      230                      235                      240

CGG  ATG  GGA  ATG  TCC  TTT  GGT  CTG  GAG  TCA  GGC  AAA  TGC  TCT  CTG  GAG          768
Arg  Met  Gly  Met  Ser  Phe  Gly  Leu  Glu  Ser  Gly  Lys  Cys  Ser  Leu  Glu
                         245                      250                      255

GAT  CTG  AAA  ATC  GCA  AGA  TCC  CTG  GTT  CCA  AAA  GCT  TTA  GAA  GGC  TAT          816
Asp  Leu  Lys  Ile  Ala  Arg  Ser  Leu  Val  Pro  Lys  Ala  Leu  Glu  Gly  Tyr
               260                      265                      270

ATT  ACA  GAT  ATC  TCC  ACA  GGA  CCT  TCT  TGG  TTA  AAT  CAG  GGA  CTA  CTT          864
Ile  Thr  Asp  Ile  Ser  Thr  Gly  Pro  Ser  Trp  Leu  Asn  Gln  Gly  Leu  Leu
          275                      280                      285

TTG  AAC  TCT  ACC  CAA  TCA  GTT  TCA  AAT  TTA  GAC  CCG  ACC  ACC  GGT  GCC          912
Leu  Asn  Ser  Thr  Gln  Ser  Val  Ser  Asn  Leu  Asp  Pro  Thr  Thr  Gly  Ala
290                      295                      300

ACT  GTA  CCC  CAA  TCA  AGT  GTA  AAC  CAA  GGG  TTG  TGC  TTG  GAT  GCT  GAA          960
Thr  Val  Pro  Gln  Ser  Ser  Val  Asn  Gln  Gly  Leu  Cys  Leu  Asp  Ala  Glu
305                      310                      315                      320

GTG  GCC  TTA  GCA  ACT  GGG  CAG  CTC  CCT  GCC  TCA  AAC  AGT  CAC  CAG  TCC         1008
Val  Ala  Leu  Ala  Thr  Gly  Gln  Leu  Pro  Ala  Ser  Asn  Ser  His  Gln  Ser
                         325                      330                      335

AGC  AGT  GCA  GCC  TCT  CAC  TTC  TCG  GAG  TCC  CGC  GGC  GAG  ACC  CCC  TGT         1056
Ser  Ser  Ala  Ala  Ser  His  Phe  Ser  Glu  Ser  Arg  Gly  Glu  Thr  Pro  Cys
               340                      345                      350

TCA  TTC  AAC  GAT  GAA  GAT  GAG  GAA  GAT  GAA  GAG  GAG  GAT  CCC  TCC  TCC         1104
Ser  Phe  Asn  Asp  Glu  Asp  Glu  Glu  Asp  Glu  Glu  Glu  Asp  Pro  Ser  Ser
          355                      360                      365

CCA  GAA  TAAAGACAGG  AGAGAACTCA  TGTTTTAAAA  AAAAAAAAAA  ACTCGAG                       1157
Pro  Glu
     370
```

( 2 ) INFORMATION FOR SEQ ID NO:6:

( i ) SEQUENCE CHARACTERISTICS:
        ( A ) LENGTH: 370 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ile  Ile  Ser  Thr  Pro  Gln  Arg  Ile  Ala  Asn  Ser  Gly  Ser  Val  Leu
1                   5                        10                       15

Ile  Gly  Asn  Pro  Tyr  Thr  Pro  Ala  Pro  Ala  Met  Val  Thr  Gln  Thr  His
               20                       25                       30
```

```
Ile  Ala  Glu  Ala  Ala  Gly  Trp  Val  Pro  Ser  Lys  Arg  Ser  Lys  Lys  Gly
          35                      40                       45
Asp  Lys  Asn  Gly  Lys  Gly  Leu  Arg  His  Phe  Ser  Met  Lys  Val  Cys  Glu
     50                       55                       60
Lys  Val  Gln  Arg  Lys  Gly  Thr  Thr  Ser  Tyr  Asn  Glu  Val  Ala  Asp  Glu
65                       70                       75                       80
Leu  Val  Ser  Glu  Phe  Thr  Asn  Ser  Asn  Asn  His  Leu  Ala  Ala  Asp  Ser
                    85                       90                       95
Gln  Ala  Tyr  Asp  Gln  Glu  Asn  Ile  Arg  Arg  Val  Tyr  Asp  Ala  Leu
                    100                      105                     110
Asn  Val  Leu  Met  Ala  Met  Asn  Ile  Ile  Ser  Lys  Glu  Lys  Lys  Glu  Ile
               115                      120                     125
Lys  Trp  Ile  Gly  Leu  Pro  Thr  Asn  Ser  Ala  Gln  Glu  Cys  Gln  Asn  Leu
     130                      135                     140
Glu  Ile  Glu  Lys  Gln  Arg  Arg  Ile  Glu  Arg  Ile  Lys  Gln  Lys  Arg  Ala
145                      150                      155                     160
Gln  Leu  Gln  Glu  Leu  Leu  Leu  Gln  Gln  Ile  Ala  Phe  Lys  Asn  Leu  Val
                    165                      170                     175
Gln  Arg  Asn  Arg  Gln  Asn  Glu  Gln  Gln  Asn  Gln  Gly  Pro  Pro  Ala  Val
               180                      185                     190
Asn  Ser  Thr  Ile  Gln  Leu  Pro  Phe  Ile  Ile  Ile  Asn  Thr  Ser  Arg  Lys
          195                      200                      205
Thr  Val  Ile  Asp  Cys  Ser  Ile  Ser  Ser  Asp  Lys  Phe  Glu  Tyr  Leu  Phe
     210                      215                      220
Asn  Phe  Asp  Asn  Thr  Phe  Glu  Ile  His  Asp  Asp  Ile  Glu  Val  Leu  Lys
225                      230                      235                     240
Arg  Met  Gly  Met  Ser  Phe  Gly  Leu  Glu  Ser  Gly  Lys  Cys  Ser  Leu  Glu
                    245                      250                     255
Asp  Leu  Lys  Ile  Ala  Arg  Ser  Leu  Val  Pro  Lys  Ala  Leu  Glu  Gly  Tyr
               260                      265                     270
Ile  Thr  Asp  Ile  Ser  Thr  Gly  Pro  Ser  Trp  Leu  Asn  Gln  Gly  Leu  Leu
          275                      280                      285
Leu  Asn  Ser  Thr  Gln  Ser  Val  Ser  Asn  Leu  Asp  Pro  Thr  Thr  Gly  Ala
     290                      295                      300
Thr  Val  Pro  Gln  Ser  Ser  Val  Asn  Gln  Gly  Leu  Cys  Leu  Asp  Ala  Glu
305                      310                      315                     320
Val  Ala  Leu  Ala  Thr  Gly  Gln  Leu  Pro  Ala  Ser  Asn  Ser  His  Gln  Ser
                    325                      330                     335
Ser  Ser  Ala  Ala  Ser  His  Phe  Ser  Glu  Ser  Arg  Gly  Glu  Thr  Pro  Cys
               340                      345                     350
Ser  Phe  Asn  Asp  Glu  Asp  Glu  Glu  Asp  Glu  Glu  Glu  Asp  Pro  Ser  Ser
          355                      360                      365
Pro  Glu
     370
```

( 2 ) INFORMATION FOR SEQ ID NO:7:

( i ) SEQUENCE CHARACTERISTICS:
        ( A ) LENGTH: 1202 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1155

( x i ) SEQUENCE DESCRIPTION: SEQ ID NO:7:

| ATG | ATT | ATA | AGC | ACA | CCG | CAG | AGA | ATT | GCC | AAT | TCA | GGA | AGT | GTT | CTG | 48 |
|---|---|---|---|---|---|---|---|---|---|---|---|---|---|---|---|---|
| Met | Ile | Ile | Ser | Thr | Pro | Gln | Arg | Ile | Ala | Asn | Ser | Gly | Ser | Val | Leu | |
| 1 | | | | 5 | | | | | 10 | | | | | 15 | | |

| ATT | GGG | AAT | CCA | TAT | ACC | CCT | GCA | CCC | GCA | ATG | GTC | ACT | CAG | ACT | CAC | 96 |
|---|---|---|---|---|---|---|---|---|---|---|---|---|---|---|---|---|
| Ile | Gly | Asn | Pro | Tyr | Thr | Pro | Ala | Pro | Ala | Met | Val | Thr | Gln | Thr | His | |
| | | | 20 | | | | | 25 | | | | | 30 | | | |

| ATA | GCT | GAG | GCT | GCT | GGC | TGG | GTT | CCC | AGT | GAT | AGA | AAA | CGA | GCT | AGA | 144 |
|---|---|---|---|---|---|---|---|---|---|---|---|---|---|---|---|---|
| Ile | Ala | Glu | Ala | Ala | Gly | Trp | Val | Pro | Ser | Asp | Arg | Lys | Arg | Ala | Arg | |
| | | | 35 | | | | | 40 | | | | | 45 | | | |

| GAA | TTT | ATA | GAC | TCT | GAT | TTT | TCA | GAA | AGT | AAA | CGA | AGC | AAA | AAA | GGA | 192 |
|---|---|---|---|---|---|---|---|---|---|---|---|---|---|---|---|---|
| Glu | Phe | Ile | Asp | Ser | Asp | Phe | Ser | Glu | Ser | Lys | Arg | Ser | Lys | Lys | Gly | |
| | | 50 | | | | | 55 | | | | | 60 | | | | |

| GAT | AAA | AAT | GGG | AAA | GGC | TTG | AGA | CAT | TTT | TCA | ATG | AAG | GTG | TGT | GAG | 240 |
|---|---|---|---|---|---|---|---|---|---|---|---|---|---|---|---|---|
| Asp | Lys | Asn | Gly | Lys | Gly | Leu | Arg | His | Phe | Ser | Met | Lys | Val | Cys | Glu | |
| 65 | | | | | 70 | | | | | 75 | | | | | 80 | |

| AAA | GTT | CAG | CGG | AAA | GGC | ACA | ACT | TCA | TAC | AAT | GAG | GTA | GCT | GAT | GAG | 288 |
|---|---|---|---|---|---|---|---|---|---|---|---|---|---|---|---|---|
| Lys | Val | Gln | Arg | Lys | Gly | Thr | Thr | Ser | Tyr | Asn | Glu | Val | Ala | Asp | Glu | |
| | | | | 85 | | | | | 90 | | | | | 95 | | |

| CTG | GTA | TCT | GAG | TTT | ACC | AAC | TCA | AAT | AAC | CAT | CTG | GCA | GCT | GAT | TCG | 336 |
|---|---|---|---|---|---|---|---|---|---|---|---|---|---|---|---|---|
| Leu | Val | Ser | Glu | Phe | Thr | Asn | Ser | Asn | Asn | His | Leu | Ala | Ala | Asp | Ser | |
| | | | 100 | | | | | 105 | | | | | 110 | | | |

| GCT | TAT | GAT | CAG | GAG | AAC | ATT | AGA | CGA | AGA | GTT | TAT | GAT | GCT | TTA | AAT | 384 |
|---|---|---|---|---|---|---|---|---|---|---|---|---|---|---|---|---|
| Ala | Tyr | Asp | Gln | Glu | Asn | Ile | Arg | Arg | Arg | Val | Tyr | Asp | Ala | Leu | Asn | |
| | | 115 | | | | | 120 | | | | | 125 | | | | |

| GTA | CTA | ATG | GCG | ATG | AAC | ATA | ATT | TCA | AAG | GAA | AAA | AAA | GAA | ATC | AAG | 432 |
|---|---|---|---|---|---|---|---|---|---|---|---|---|---|---|---|---|
| Val | Leu | Met | Ala | Met | Asn | Ile | Ile | Ser | Lys | Glu | Lys | Lys | Glu | Ile | Lys | |
| | | 130 | | | | | 135 | | | | | 140 | | | | |

| TGG | ATT | GGC | CTG | CCT | ACC | AAT | TCT | GCT | CAG | GAA | TGC | CAG | AAC | CTG | GAA | 480 |
|---|---|---|---|---|---|---|---|---|---|---|---|---|---|---|---|---|
| Trp | Ile | Gly | Leu | Pro | Thr | Asn | Ser | Ala | Gln | Glu | Cys | Gln | Asn | Leu | Glu | |
| 145 | | | | | 150 | | | | | 155 | | | | | 160 | |

| ATC | GAG | AAG | CAG | AGG | CGG | ATA | GAA | CGG | ATA | AAG | CAG | AAG | CGA | GCC | CAG | 528 |
|---|---|---|---|---|---|---|---|---|---|---|---|---|---|---|---|---|
| Ile | Glu | Lys | Gln | Arg | Arg | Ile | Glu | Arg | Ile | Lys | Gln | Lys | Arg | Ala | Gln | |
| | | | | 165 | | | | | 170 | | | | | 175 | | |

| CTA | CAA | GAA | CTT | CTC | CTT | CAG | CAA | ATT | GCT | TTT | AAA | AAC | CTG | GTA | CAG | 576 |
|---|---|---|---|---|---|---|---|---|---|---|---|---|---|---|---|---|
| Leu | Gln | Glu | Leu | Leu | Leu | Gln | Gln | Ile | Ala | Phe | Lys | Asn | Leu | Val | Gln | |
| | | | 180 | | | | | 185 | | | | | 190 | | | |

| AGA | AAT | CGA | CAA | AAT | GAA | CAA | CAA | AAC | CAG | GGC | CCT | CCA | GCT | GTG | AAT | 624 |
|---|---|---|---|---|---|---|---|---|---|---|---|---|---|---|---|---|
| Arg | Asn | Arg | Gln | Asn | Glu | Gln | Gln | Asn | Gln | Gly | Pro | Pro | Ala | Val | Asn | |
| | | 195 | | | | | 200 | | | | | 205 | | | | |

| TCC | ACC | ATT | CAG | CTG | CCA | TTT | ATA | ATC | ATT | AAT | ACA | AGC | AGG | AAA | ACA | 672 |
|---|---|---|---|---|---|---|---|---|---|---|---|---|---|---|---|---|
| Ser | Thr | Ile | Gln | Leu | Pro | Phe | Ile | Ile | Ile | Asn | Thr | Ser | Arg | Lys | Thr | |
| | 210 | | | | | 215 | | | | | 220 | | | | | |

| GTC | ATA | GAC | TGC | AGC | ATC | TCC | AGT | GAC | AAA | TTT | GAA | TAC | CTT | TTT | AAT | 720 |
|---|---|---|---|---|---|---|---|---|---|---|---|---|---|---|---|---|
| Val | Ile | Asp | Cys | Ser | Ile | Ser | Ser | Asp | Lys | Phe | Glu | Tyr | Leu | Phe | Asn | |
| 225 | | | | | 230 | | | | | 235 | | | | | 240 | |

| TTT | GAT | AAC | ACC | TTT | GAG | ATC | CAC | GAC | GAC | ATA | GAG | GTA | CTG | AAG | CGG | 768 |
|---|---|---|---|---|---|---|---|---|---|---|---|---|---|---|---|---|
| Phe | Asp | Asn | Thr | Phe | Glu | Ile | His | Asp | Asp | Ile | Glu | Val | Leu | Lys | Arg | |
| | | | 245 | | | | | 250 | | | | | 255 | | | |

| ATG | GGA | ATG | TCC | TTT | GGT | CTG | GAG | TCA | GGC | AAA | TGC | TCT | CTG | GAG | GAT | 816 |
|---|---|---|---|---|---|---|---|---|---|---|---|---|---|---|---|---|
| Met | Gly | Met | Ser | Phe | Gly | Leu | Glu | Ser | Gly | Lys | Cys | Ser | Leu | Glu | Asp | |
| | | | 260 | | | | | 265 | | | | | 270 | | | |

| CTG | AAA | ATC | GCA | AGA | TCC | CTG | GTT | CCA | AAA | GCT | TTA | GAA | GGC | TAT | ATT | 864 |
|---|---|---|---|---|---|---|---|---|---|---|---|---|---|---|---|---|
| Leu | Lys | Ile | Ala | Arg | Ser | Leu | Val | Pro | Lys | Ala | Leu | Glu | Gly | Tyr | Ile | |
| | | 275 | | | | | 280 | | | | | 285 | | | | |

| ACA | GAT | ATC | TCC | ACA | GGA | CCT | TCT | TGG | TTA | AAT | CAG | GGA | CTA | CTT | TTG | 912 |
|---|---|---|---|---|---|---|---|---|---|---|---|---|---|---|---|---|
| Thr | Asp | Ile | Ser | Thr | Gly | Pro | Ser | Trp | Leu | Asn | Gln | Gly | Leu | Leu | Leu | |
| | 290 | | | | | 295 | | | | | 300 | | | | | |

| AAC | TCT | ACC | CAA | TCA | GTT | TCA | AAT | TTA | GAC | CCG | ACC | ACC | GGT | GCC | ACT | 960 |

```
Asn  Ser  Thr  Gln  Ser  Val  Ser  Asn  Leu  Asp  Pro  Thr  Thr  Gly  Ala  Thr
305                 310                 315                      320

GTA  CCC  CAA  TCA  AGT  GTA  AAC  CAA  GGG  TTG  TGC  TTG  GAT  GCT  GAA  GTG      1008
Val  Pro  Gln  Ser  Ser  Val  Asn  Gln  Gly  Leu  Cys  Leu  Asp  Ala  Glu  Val
                    325                 330                      335

GCC  TTA  GCA  ACT  GGG  CAG  CTC  CCT  GCC  TCA  AAC  AGT  CAC  CAG  TCC  AGC      1056
Ala  Leu  Ala  Thr  Gly  Gln  Leu  Pro  Ala  Ser  Asn  Ser  His  Gln  Ser  Ser
               340                      345                      350

AGT  GCA  GCC  TCT  CAC  TTC  TCG  GAG  TCC  CGC  GGC  GAG  ACC  CCC  TGT  TCA      1104
Ser  Ala  Ala  Ser  His  Phe  Ser  Glu  Ser  Arg  Gly  Glu  Thr  Pro  Cys  Ser
               355            360                      365

TTC  AAC  GAT  GAA  GAT  GAG  GAA  GAT  GAA  GAG  GAG  GAT  CCC  TCC  TCC  CCA      1152
Phe  Asn  Asp  Glu  Asp  Glu  Glu  Asp  Glu  Glu  Glu  Asp  Pro  Ser  Ser  Pro
          370                 375                      380

GAA  TAAAGACAGG  AGAGAACTCA  TGTTTTAAAA  AAAAAAAAAA  ACTCGAG                        1202
Glu
385
```

( 2 ) INFORMATION FOR SEQ ID NO:8:

( i ) SEQUENCE CHARACTERISTICS:
        ( A ) LENGTH: 385 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Ile  Ile  Ser  Thr  Pro  Gln  Arg  Ile  Ala  Asn  Ser  Gly  Ser  Val  Leu
1                   5                   10                      15

Ile  Gly  Asn  Pro  Tyr  Thr  Pro  Ala  Pro  Ala  Met  Val  Thr  Gln  Thr  His
               20                  25                           30

Ile  Ala  Glu  Ala  Ala  Gly  Trp  Val  Pro  Ser  Asp  Arg  Lys  Arg  Ala  Arg
               35                  40                       45

Glu  Phe  Ile  Asp  Ser  Asp  Phe  Ser  Glu  Ser  Lys  Arg  Ser  Lys  Lys  Gly
          50                  55                       60

Asp  Lys  Asn  Gly  Lys  Gly  Leu  Arg  His  Phe  Ser  Met  Lys  Val  Cys  Glu
65                  70                       75                           80

Lys  Val  Gln  Arg  Lys  Gly  Thr  Thr  Ser  Tyr  Asn  Glu  Val  Ala  Asp  Glu
                    85                  90                           95

Leu  Val  Ser  Glu  Phe  Thr  Asn  Ser  Asn  Asn  His  Leu  Ala  Ala  Asp  Ser
                    100                 105                      110

Ala  Tyr  Asp  Gln  Glu  Asn  Ile  Arg  Arg  Arg  Val  Tyr  Asp  Ala  Leu  Asn
               115                      120                      125

Val  Leu  Met  Ala  Met  Asn  Ile  Ile  Ser  Lys  Glu  Lys  Lys  Glu  Ile  Lys
          130                      135                      140

Trp  Ile  Gly  Leu  Pro  Thr  Asn  Ser  Ala  Gln  Glu  Cys  Gln  Asn  Leu  Glu
145                      150                      155                      160

Ile  Glu  Lys  Gln  Arg  Arg  Ile  Glu  Arg  Ile  Lys  Gln  Lys  Arg  Ala  Gln
                    165                      170                      175

Leu  Gln  Glu  Leu  Leu  Leu  Gln  Gln  Ile  Ala  Phe  Lys  Asn  Leu  Val  Gln
               180                      185                      190

Arg  Asn  Arg  Gln  Asn  Glu  Gln  Gln  Asn  Gln  Gly  Pro  Pro  Ala  Val  Asn
          195                      200                      205

Ser  Thr  Ile  Gln  Leu  Pro  Phe  Ile  Ile  Ile  Asn  Thr  Ser  Arg  Lys  Thr
     210                      215                      220

Val  Ile  Asp  Cys  Ser  Ile  Ser  Ser  Asp  Lys  Phe  Glu  Tyr  Leu  Phe  Asn
225                      230                      235                      240
```

```
Phe  Asp  Asn  Thr  Phe  Glu  Ile  His  Asp  Asp  Ile  Glu  Val  Leu  Lys  Arg
               245                 250                      255

Met  Gly  Met  Ser  Phe  Gly  Leu  Glu  Ser  Gly  Lys  Cys  Ser  Leu  Glu  Asp
               260                 265                      270

Leu  Lys  Ile  Ala  Arg  Ser  Leu  Val  Pro  Lys  Ala  Leu  Glu  Gly  Tyr  Ile
               275                 280                      285

Thr  Asp  Ile  Ser  Thr  Gly  Pro  Ser  Trp  Leu  Asn  Gln  Gly  Leu  Leu  Leu
               290                 295                      300

Asn  Ser  Thr  Gln  Ser  Val  Ser  Asn  Leu  Asp  Pro  Thr  Thr  Gly  Ala  Thr
305                           310                 315                      320

Val  Pro  Gln  Ser  Ser  Val  Asn  Gln  Gly  Leu  Cys  Leu  Asp  Ala  Glu  Val
                         325                 330                      335

Ala  Leu  Ala  Thr  Gly  Gln  Leu  Pro  Ala  Ser  Asn  Ser  His  Gln  Ser  Ser
               340                 345                      350

Ser  Ala  Ala  Ser  His  Phe  Ser  Glu  Ser  Arg  Gly  Glu  Thr  Pro  Cys  Ser
               355                 360                      365

Phe  Asn  Asp  Glu  Asp  Glu  Glu  Asp  Glu  Glu  Glu  Asp  Pro  Ser  Ser  Pro
     370                      375                      380

Glu
385
```

( 2 ) INFORMATION FOR SEQ ID NO:9:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:9:

```
Ser  Asp  Arg  Lys  Arg  Ala  Arg  Glu  Phe  Ile  Asp  Ser  Asp  Phe  Ser  Glu
1                   5                        10                      15
```

( 2 ) INFORMATION FOR SEQ ID NO:10:

( i ) SEQUENCE CHARACTERISTICS:
        ( A ) LENGTH: 410 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:10:

```
Met  Ala  Lys  Asp  Ala  Gly  Leu  Ile  Glu  Ala  Asn  Gly  Glu  Leu  Lys  Val
1                   5                        10                      15

Phe  Ile  Asp  Gln  Asn  Leu  Ser  Pro  Gly  Lys  Gly  Val  Val  Ser  Leu  Val
                    20                       25                      30

Ala  Val  His  Pro  Ser  Thr  Val  Asn  Pro  Leu  Gly  Lys  Gln  Leu  Leu  Pro
               35                  40                       45

Lys  Thr  Phe  Gly  Gln  Ser  Asn  Val  Asn  Ile  Ala  Gln  Gln  Val  Val  Ile
          50                       55                       60

Gly  Thr  Pro  Gln  Arg  Pro  Ala  Ala  Ser  Asn  Thr  Leu  Val  Val  Gly  Ser
65                       70                       75                        80

Pro  His  Thr  Pro  Ser  Thr  His  Phe  Ala  Ser  Gln  Asn  Gln  Pro  Ser  Asp
                    85                       90                       95

Ser  Ser  Pro  Trp  Ser  Ala  Gly  Lys  Arg  Asn  Arg  Lys  Gly  Glu  Lys  Asn
               100                      105                      110
```

|   |   |   |   |   |   |   |   |   |   |   |   |   |   |   |
|---|---|---|---|---|---|---|---|---|---|---|---|---|---|---|
| Gly | Lys | Gly | Leu | Arg | His | Phe | Ser | Met | Lys | Val | Cys | Glu | Lys | Val | Gln |
|  |  | 115 |  |  |  |  | 120 |  |  |  |  | 125 |  |  |  |
| Arg | Lys | Gly | Thr | Thr | Ser | Tyr | Asn | Glu | Val | Ala | Asp | Glu | Leu | Val | Ala |
|  | 130 |  |  |  |  | 135 |  |  |  |  | 140 |  |  |  |  |
| Glu | Phe | Ser | Ala | Ala | Asp | Asn | His | Ile | Leu | Pro | Asn | Glu | Ser | Ala | Tyr |
| 145 |  |  |  |  | 150 |  |  |  |  | 155 |  |  |  |  | 160 |
| Asp | Gln | Lys | Asn | Ile | Arg | Arg | Arg | Val | Tyr | Asp | Ala | Leu | Asn | Val | Leu |
|  |  |  |  | 165 |  |  |  |  | 170 |  |  |  |  | 175 |  |
| Met | Ala | Met | Asn | Ile | Ile | Ser | Lys | Glu | Lys | Lys | Glu | Ile | Lys | Trp | Ile |
|  |  |  | 180 |  |  |  |  | 185 |  |  |  |  | 190 |  |  |
| Gly | Leu | Pro | Thr | Asn | Ser | Ala | Gln | Glu | Cys | Gln | Asn | Leu | Glu | Val | Glu |
|  |  | 195 |  |  |  |  | 200 |  |  |  |  | 205 |  |  |  |
| Arg | Gln | Arg | Arg | Leu | Glu | Arg | Ile | Lys | Gln | Lys | Gln | Ser | Gln | Leu | Gln |
|  | 210 |  |  |  |  | 215 |  |  |  |  | 220 |  |  |  |  |
| Glu | Leu | Ile | Leu | Gln | Gln | Ile | Ala | Phe | Lys | Asn | Leu | Val | Gln | Arg | Asn |
| 225 |  |  |  |  | 230 |  |  |  |  | 235 |  |  |  |  | 240 |
| Arg | His | Ala | Glu | Gln | Gln | Ala | Ser | Arg | Pro | Pro | Pro | Pro | Asn | Ser | Val |
|  |  |  |  | 245 |  |  |  |  | 250 |  |  |  |  | 255 |  |
| Ile | His | Leu | Pro | Phe | Ile | Ile | Val | Asn | Thr | Ser | Lys | Lys | Thr | Val | Ile |
|  |  |  | 260 |  |  |  |  | 265 |  |  |  |  | 270 |  |  |
| Asp | Cys | Ser | Ile | Ser | Asn | Asp | Lys | Phe | Glu | Tyr | Leu | Phe | Asn | Phe | Asp |
|  |  | 275 |  |  |  |  | 280 |  |  |  |  | 285 |  |  |  |
| Asn | Thr | Phe | Glu | Ile | His | Asp | Asp | Ile | Glu | Val | Leu | Lys | Arg | Met | Gly |
|  | 290 |  |  |  |  | 295 |  |  |  |  | 300 |  |  |  |  |
| Met | Ala | Cys | Gly | Leu | Glu | Ser | Gly | Ser | Cys | Ser | Ala | Glu | Asp | Leu | Lys |
| 305 |  |  |  |  | 310 |  |  |  |  | 315 |  |  |  |  | 320 |
| Met | Ala | Arg | Ser | Leu | Val | Pro | Lys | Ala | Leu | Glu | Pro | Tyr | Val | Thr | Glu |
|  |  |  |  | 325 |  |  |  |  | 330 |  |  |  |  | 335 |  |
| Met | Ala | Gln | Gly | Thr | Val | Gly | Gly | Val | Phe | Ile | Thr | Thr | Ala | Gly | Ser |
|  |  |  | 340 |  |  |  |  | 345 |  |  |  |  | 350 |  |  |
| Thr | Ser | Asn | Gly | Thr | Arg | Phe | Ser | Ala | Ser | Asp | Leu | Thr | Asn | Gly | Ala |
|  |  | 355 |  |  |  |  | 360 |  |  |  |  | 365 |  |  |  |
| Asp | Gly | Met | Leu | Ala | Thr | Ser | Ser | Asn | Gly | Ser | Gln | Tyr | Ser | Gly | Ser |
|  | 370 |  |  |  |  | 375 |  |  |  |  | 380 |  |  |  |  |
| Arg | Val | Glu | Thr | Pro | Val | Ser | Tyr | Val | Gly | Glu | Asp | Asp | Glu | Glu | Asp |
| 385 |  |  |  |  | 390 |  |  |  |  | 395 |  |  |  |  | 400 |
| Asp | Asp | Phe | Asn | Glu | Asn | Asp | Glu | Asp | Asp |  |  |  |  |  |  |
|  |  |  |  | 405 |  |  |  |  | 410 |  |  |  |  |  |  |

( 2 ) INFORMATION FOR SEQ ID NO:11:

( i ) SEQUENCE CHARACTERISTICS:
        ( A ) LENGTH: 410 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:11:

|   |   |   |   |   |   |   |   |   |   |   |   |   |   |   |   |
|---|---|---|---|---|---|---|---|---|---|---|---|---|---|---|---|
| Met | Ala | Lys | Asp | Ala | Ser | Leu | Ile | Glu | Ala | Asn | Gly | Glu | Leu | Lys | Val |
| 1 |  |  |  | 5 |  |  |  |  | 10 |  |  |  |  | 15 |  |
| Phe | Ile | Asp | Gln | Asn | Leu | Ser | Pro | Gly | Lys | Gly | Val | Val | Ser | Leu | Val |
|  |  |  | 20 |  |  |  |  | 25 |  |  |  |  | 30 |  |  |
| Ala | Val | His | Pro | Ser | Thr | Val | Asn | Thr | Leu | Gly | Lys | Gln | Leu | Leu | Pro |
|  |  | 35 |  |  |  |  | 40 |  |  |  |  | 45 |  |  |  |
| Lys | Thr | Phe | Gly | Gln | Ser | Asn | Val | Asn | Ile | Thr | Gln | Gln | Val | Val | Ile |

|   | 50 |   |   |   | 55 |   |   |   | 60 |   |   |   |
|---|---|---|---|---|---|---|---|---|---|---|---|---|

Gly Thr Pro Gln Arg Pro Ala Ala Ser Asn Thr Ile Val Val Gly Ser
65                      70                          75                              80

Pro His Thr Pro Asn Thr His Phe Val Ser Gln Asn Gln Thr Ser Asp
                    85                      90                          95

Ser Ser Pro Trp Ser Ala Gly Lys Arg Asn Arg Lys Gly Glu Lys Asn
                100                     105                     110

Gly Lys Gly Leu Arg His Phe Ser Met Lys Val Cys Glu Lys Val Gln
            115                     120                     125

Arg Lys Gly Thr Thr Ser Tyr Asn Glu Val Ala Asp Glu Leu Val Ala
        130                     135                 140

Glu Phe Ser Ala Ala Asp Asn His Ile Leu Pro Asn Glu Ser Ala Tyr
145                     150                     155                         160

Asp Gln Lys Asn Ile Arg Arg Arg Val Tyr Asp Ala Leu Asn Val Leu
                    165                     170                     175

Met Ala Met Asn Ile Ile Ser Lys Glu Lys Lys Glu Ile Lys Trp Ile
            180                     185                     190

Gly Leu Pro Thr Asn Ser Ala Gln Glu Cys Gln Asn Leu Glu Val Glu
        195                     200                     205

Arg Gln Arg Arg Leu Glu Arg Ile Lys Gln Lys Gln Ser Gln Leu Gln
        210                     215                     220

Glu Leu Ile Leu Gln Gln Ile Ala Phe Lys Asn Leu Val Gln Arg Asn
225                     230                     235                         240

Arg Gln Ala Glu Gln Gln Ala Arg Arg Pro Pro Pro Asn Ser Val
                    245                     250                     255

Ile His Leu Pro Phe Ile Ile Val Asn Thr Ser Arg Lys Thr Val Ile
            260                     265                     270

Asp Cys Ser Ile Ser Asn Asp Lys Phe Glu Tyr Leu Phe Asn Phe Asp
        275                     280                     285

Asn Thr Phe Glu Ile His Asp Asp Ile Glu Val Leu Lys Arg Met Gly
    290                     295                     300

Met Ala Cys Gly Leu Glu Ser Gly Asn Cys Ser Ala Glu Asp Leu Lys
305                     310                     315                         320

Val Ala Arg Ser Leu Val Pro Lys Ala Leu Glu Pro Tyr Val Thr Glu
                325                     330                     335

Met Ala Gln Gly Ser Ile Gly Gly Val Phe Val Thr Thr Thr Gly Ser
            340                     345                     350

Thr Ser Asn Gly Thr Arg Leu Ser Ala Ser Asp Leu Ser Asn Gly Ala
        355                     360                     365

Asp Gly Met Leu Ala Thr Ser Ser Asn Gly Ser Gln Tyr Ser Gly Ser
    370                     375                     380

Arg Val Glu Thr Pro Val Ser Tyr Val Gly Glu Asp Asp Asp Asp
385                     390                     395                         400

Asp Asp Phe Asn Glu Asn Asp Glu Glu Asp
                    405                     410

(2) INFORMATION FOR SEQ ID NO:12:

(i) SEQUENCE CHARACTERISTICS:
        (A) LENGTH: 2457 base pairs
        (B) TYPE: nucleic acid
        (C) STRANDEDNESS: single
        (D) TOPOLOGY: linear (ii) MOLECULE TYPE: cDNA (ix) FEATURE:

-continued ( A ) NAME/KEY: CDS
( B ) LOCATION: 87..1397

( x i ) SEQUENCE DESCRIPTION: SEQ ID NO:12:

```
GGGATCGAGC CCTCGCCGAG GCCTGCCGCC ATGGGCCCGC GCCGCCGCCG CCGCCTGTCA            60

CCCGGGCCGC GCGGGCCGTG AGCGTC ATG GCC TTG GCC GGG GCC CCT GCG GGC           113
                              Met Ala Leu Ala Gly Ala Pro Ala Gly
                                1               5

GGC CCA TGC GCG CCG GCG CTG GAG GCC CTG CTC GGG GCC GGC GCG CTG            161
Gly Pro Cys Ala Pro Ala Leu Glu Ala Leu Leu Gly Ala Gly Ala Leu
 10              15                  20                  25

CGG CTG CTC GAC TCC TCG CAG ATC GTC ATC ATC TCC GCC GCG CAG GAC            209
Arg Leu Leu Asp Ser Ser Gln Ile Val Ile Ile Ser Ala Ala Gln Asp
                 30                  35                  40

GCC AGC GCC CCG CCG GCT CCC ACC GGC CCC GCG GCC CCG GCC GCC GGC            257
Ala Ser Ala Pro Pro Ala Pro Thr Gly Pro Ala Ala Pro Ala Ala Gly
             45                  50                  55

CCC TGC GAC CCT GAC CTG CTG CTC TTC GCC ACA CCG CAG GCG CCC CGG            305
Pro Cys Asp Pro Asp Leu Leu Leu Phe Ala Thr Pro Gln Ala Pro Arg
         60                  65                  70

CCC ACA CCC AGT GCG CCG CGG CCC GCG CTC GGC CGC CCG CCG GTG AAG            353
Pro Thr Pro Ser Ala Pro Arg Pro Ala Leu Gly Arg Pro Pro Val Lys
     75                  80                  85

CGG AGG CTG GAC CTG GAA ACT GAC CAT CAG TAC CTG GCC GAG AGC AGT            401
Arg Arg Leu Asp Leu Glu Thr Asp His Gln Tyr Leu Ala Glu Ser Ser
 90                  95                 100                 105

GGG CCA GCT CGG GGC AGA GGC CGC CAT CCA GGA AAA GGT GTG AAA TCC            449
Gly Pro Ala Arg Gly Arg Gly Arg His Pro Gly Lys Gly Val Lys Ser
                110                 115                 120

CCG GGG GAG AAG TCA CGC TAT GAG ACC TCA CTG AAT CTG ACC ACC AAG            497
Pro Gly Glu Lys Ser Arg Tyr Glu Thr Ser Leu Asn Leu Thr Thr Lys
            125                 130                 135

CGC TTC CTG GAG CTG CTG AGC CAC TCG GCT GAC GGT GTC GTC GAC CTG            545
Arg Phe Leu Glu Leu Leu Ser His Ser Ala Asp Gly Val Val Asp Leu
        140                 145                 150

AAC TGG GCT GCC GAG GTG CTG AAG GTG CAG AAG CGG CGC ATC TAT GAC            593
Asn Trp Ala Ala Glu Val Leu Lys Val Gln Lys Arg Arg Ile Tyr Asp
    155                 160                 165

ATC ACC AAC GTC CTT GAG GGC ATC CAG CTC ATT GCC AAG AAG TCC AAG            641
Ile Thr Asn Val Leu Glu Gly Ile Gln Leu Ile Ala Lys Lys Ser Lys
170                 175                 180                 185

AAC CAC ATC CAG TGG CTG GGC AGC CAC ACC ACA GTG GGC GTC GGC GGA            689
Asn His Ile Gln Trp Leu Gly Ser His Thr Thr Val Gly Val Gly Gly
                190                 195                 200

CGG CTT GAG GGG TTG ACC CAG GAC CTC CGA CAG CTG CAG GAG AGC GAG            737
Arg Leu Glu Gly Leu Thr Gln Asp Leu Arg Gln Leu Gln Glu Ser Glu
            205                 210                 215

CAG CAG CTG GAC CAC CTG ATG AAT ATC TGT ACT ACG CAG CTG CGC CTG            785
Gln Gln Leu Asp His Leu Met Asn Ile Cys Thr Thr Gln Leu Arg Leu
        220                 225                 230

CTC TCC GAG GAC ACT GAC AGC CAG CGC CTG GCC TAC GTG ACG TGT CAG            833
Leu Ser Glu Asp Thr Asp Ser Gln Arg Leu Ala Tyr Val Thr Cys Gln
    235                 240                 245

GAC CTT CGT AGC ATT GCA GAC CCT GCA GAG CAG ATG GTT ATG GTG ATC            881
Asp Leu Arg Ser Ile Ala Asp Pro Ala Glu Gln Met Val Met Val Ile
250                 255                 260                 265

AAA GCC CCT CCT GAG ACC CAG CTC CAA GCC GTG GAC TCT TCG GAG AAC            929
Lys Ala Pro Pro Glu Thr Gln Leu Gln Ala Val Asp Ser Ser Glu Asn
                270                 275                 280

TTT CAG ATC TCC CTT AAG AGC AAA CAA GGC CCG ATC GAT GTT TTC TG             977
```

| | | | | | | | | | | | | | | |
|---|---|---|---|---|---|---|---|---|---|---|---|---|---|---|
| Phe | Gln | Ile | Ser | Leu | Lys | Ser | Lys | Gln | Gly | Pro | Ile | Asp | Val | Phe | Leu |
| | | | 285 | | | | | 290 | | | | 295 | | | |

| TGC | CCT | GAG | GAG | ACC | GTA | GGT | GGG | ATC | AGC | CCT | GGG | AAG | ACC | CCA | TCC | 1025 |
|---|---|---|---|---|---|---|---|---|---|---|---|---|---|---|---|---|
| Cys | Pro | Glu | Glu | Thr | Val | Gly | Gly | Ile | Ser | Pro | Gly | Lys | Thr | Pro | Ser | |
| | | 300 | | | | | 305 | | | | | 310 | | | | |

| CAG | GAG | GTC | ACT | TCT | GAG | GAG | GAG | AAC | AGG | GCC | ACT | GAC | TCT | GCC | ACC | 1073 |
|---|---|---|---|---|---|---|---|---|---|---|---|---|---|---|---|---|
| Gln | Glu | Val | Thr | Ser | Glu | Glu | Glu | Asn | Arg | Ala | Thr | Asp | Ser | Ala | Thr | |
| | | | 315 | | | | | 320 | | | | | 325 | | | |

| ATA | GTG | TCA | CCA | CCA | CCA | TCA | TCT | CCC | CCC | TCA | TCC | CTC | ACC | ACA | GAT | 1121 |
|---|---|---|---|---|---|---|---|---|---|---|---|---|---|---|---|---|
| Ile | Val | Ser | Pro | Pro | Pro | Ser | Ser | Pro | Pro | Ser | Ser | Leu | Thr | Thr | Asp | |
| 330 | | | | | 335 | | | | | 340 | | | | | 345 | |

| CCC | AGC | CAG | TCT | CTA | CTC | AGC | CTG | GAG | CAA | GAA | CCG | CTG | TTG | TCC | CGG | 1169 |
|---|---|---|---|---|---|---|---|---|---|---|---|---|---|---|---|---|
| Pro | Ser | Gln | Ser | Leu | Leu | Ser | Leu | Glu | Gln | Glu | Pro | Leu | Leu | Ser | Arg | |
| | | | | 350 | | | | | 355 | | | | | 360 | | |

| ATG | GGC | AGC | CTG | CGG | GCT | CCC | GTG | GAC | GAG | GAC | CGC | CTG | TCC | CCG | CTG | 1217 |
|---|---|---|---|---|---|---|---|---|---|---|---|---|---|---|---|---|
| Met | Gly | Ser | Leu | Arg | Ala | Pro | Val | Asp | Glu | Asp | Arg | Leu | Ser | Pro | Leu | |
| | | | 365 | | | | | 370 | | | | | 375 | | | |

| GTG | GCG | GCC | GAC | TCG | CTC | CTG | GAG | CAT | GTG | CGG | GAG | GAC | TTC | TCC | GGC | 1265 |
|---|---|---|---|---|---|---|---|---|---|---|---|---|---|---|---|---|
| Val | Ala | Ala | Asp | Ser | Leu | Leu | Glu | His | Val | Arg | Glu | Asp | Phe | Ser | Gly | |
| | | 380 | | | | | 385 | | | | | 390 | | | | |

| CTC | CTC | CCT | GAG | GAG | TTC | ATC | AGC | CTT | TCC | CCA | CCC | CAC | GAG | GCC | CTC | 1313 |
|---|---|---|---|---|---|---|---|---|---|---|---|---|---|---|---|---|
| Leu | Leu | Pro | Glu | Glu | Phe | Ile | Ser | Leu | Ser | Pro | Pro | His | Glu | Ala | Leu | |
| | 395 | | | | | 400 | | | | | 405 | | | | | |

| GAC | TAC | CAC | TTC | GGC | CTC | GAG | GAG | GGC | GAG | GGC | ATC | AGA | GAC | CTC | TTC | 1361 |
|---|---|---|---|---|---|---|---|---|---|---|---|---|---|---|---|---|
| Asp | Tyr | His | Phe | Gly | Leu | Glu | Glu | Gly | Glu | Gly | Ile | Arg | Asp | Leu | Phe | |
| 410 | | | | | 415 | | | | | 420 | | | | | 425 | |

| GAC | TGT | GAC | TTT | GGG | GAC | CTC | ACC | CCC | CTG | GAT | TTC | TGACAGGGCT | 1407 |
|---|---|---|---|---|---|---|---|---|---|---|---|---|---|
| Asp | Cys | Asp | Phe | Gly | Asp | Leu | Thr | Pro | Leu | Asp | Phe | | |
| | | | | 430 | | | | | 435 | | | | |

| | | | | |
|---|---|---|---|---|
| TGGAGGGACC | AGGGTTTCCA | GAGTAGCTCA | CCTTGTCTCT | GCAGCCCTGG | AGCCCCTGT | 1467 |
| CCCTGGCCGT | CCTCCCAGCC | TGTTTGGAAA | CATTTAATTT | ATACCCCTCT | CCTCTGTCTC | 1527 |
| CAGAAGCTTC | TAGCTCTGGG | GTCTGGCTAC | CGCTAGGAGG | CTGAGCAAGC | CAGGAAGGGA | 1587 |
| AGGAGTCTGT | GTGGTGTGTA | TGTGCATGCA | GCCTACACCC | ACACGTGTGT | ACCGGGGGTG | 1647 |
| AATGTGTGTG | AGCATGTGTG | TGTGCATGTA | CCGGGGAATG | AAGGTGAACA | TACACCTCTG | 1707 |
| TGTGTGCACT | GCAGACACGC | CCCAGTGTGT | CCACATGTGT | GTGCATGAGT | CCATCTCTGC | 1767 |
| GCGTGGGGGG | GCTCTAACTG | CACTTTCGGC | CCTTTTGCTC | GTGGGGTCCC | ACAAGGCCCA | 1827 |
| GGGCAGTGCC | TGCTCCCAGA | ATCTGGTGCT | CTGACCAGGC | CAGGTGGGGA | GGCTTTGGCT | 1887 |
| GGCTGGGCGT | GTAGGACGGT | GAGAGCACTT | CTGTCTTAAA | GGTTTTTTCT | GATTGAAGCT | 1947 |
| TTAATGGAGC | GTTATTTATT | TATCGAGGCC | TCTTTGGTGA | GCCTGGGGAA | TCAGCAAAAG | 2007 |
| GGGAGGAGGG | GTGTGGGGTT | GATACCCCAA | CTCCCTCTAC | CCTTGAGCAA | GGGCAGGGGT | 2067 |
| CCCTGAGCTG | TTCTTCTGCC | CCATACTGAA | GGAACTGAGG | CCTGGGTGAT | TTATTTATTG | 2127 |
| GGAAAGTGAG | GGAGGGAGAC | AGACTGACTG | ACAGCCATGG | GTGGTCAGAT | GGTGGGGTGG | 2187 |
| GCCCTCTCCA | GGGGCCAGT | TCAGGGCCCA | GCTGCCCCCC | AGGATGGATA | TGAGATGGGA | 2247 |
| GAGGTGAGTG | GGGGACCTTC | ACTGATGTGG | GCAGGAGGGG | TGGTGAAGGC | CTCCCCCAGC | 2307 |
| CCAGACCCTG | TGGTCCCTCC | TGCAGTGTCT | GAAGCGCCTG | CCTCCCACT | GCTCTGCCCC | 2367 |
| ACCCTCCAAT | CTGCACTTTG | ATTTGCTTCC | TAACAGCTCT | GTTCCCTCCT | GCTTTGGTTT | 2427 |
| TAATAAATAT | TTTGATGACG | TTAAAAAAAA | | | | 2457 |

( 2 ) INFORMATION FOR SEQ ID NO:13:

( i ) SEQUENCE CHARACTERISTICS:
        ( A ) LENGTH: 437 amino acids (B) TYPE: amino acid
(D) TOPOLOGY: linear (ii) MOLECULE TYPE: protein (xi) SEQUENCE DESCRIPTION: SEQ ID NO:13:

| Met | Ala | Leu | Ala | Gly | Ala | Pro | Ala | Gly | Gly | Pro | Cys | Ala | Pro | Ala | Leu |
|---|---|---|---|---|---|---|---|---|---|---|---|---|---|---|---|
| 1 | | | | 5 | | | | | 10 | | | | | 15 | |
| Glu | Ala | Leu | Leu | Gly | Ala | Gly | Ala | Leu | Arg | Leu | Leu | Asp | Ser | Ser | Gln |
| | | | 20 | | | | | 25 | | | | | 30 | | |
| Ile | Val | Ile | Ile | Ser | Ala | Ala | Gln | Asp | Ala | Ser | Ala | Pro | Pro | Ala | Pro |
| | | 35 | | | | | 40 | | | | | 45 | | | |
| Thr | Gly | Pro | Ala | Ala | Pro | Ala | Ala | Gly | Pro | Cys | Asp | Pro | Asp | Leu | Leu |
| | 50 | | | | | 55 | | | | | 60 | | | | |
| Leu | Phe | Ala | Thr | Pro | Gln | Ala | Pro | Arg | Pro | Thr | Pro | Ser | Ala | Pro | Arg |
| 65 | | | | | 70 | | | | | 75 | | | | | 80 |
| Pro | Ala | Leu | Gly | Arg | Pro | Pro | Val | Lys | Arg | Arg | Leu | Asp | Leu | Glu | Thr |
| | | | | 85 | | | | | 90 | | | | | 95 | |
| Asp | His | Gln | Tyr | Leu | Ala | Glu | Ser | Ser | Gly | Pro | Ala | Arg | Gly | Arg | Gly |
| | | | | 100 | | | | | 105 | | | | | 110 | |
| Arg | His | Pro | Gly | Lys | Gly | Val | Lys | Ser | Pro | Gly | Glu | Lys | Ser | Arg | Tyr |
| | | | 115 | | | | | 120 | | | | | 125 | | |
| Glu | Thr | Ser | Leu | Asn | Leu | Thr | Thr | Lys | Arg | Phe | Leu | Glu | Leu | Leu | Ser |
| | | 130 | | | | | 135 | | | | | 140 | | | |
| His | Ser | Ala | Asp | Gly | Val | Val | Asp | Leu | Asn | Trp | Ala | Ala | Glu | Val | Leu |
| 145 | | | | | 150 | | | | | 155 | | | | | 160 |
| Lys | Val | Gln | Lys | Arg | Arg | Ile | Tyr | Asp | Ile | Thr | Asn | Val | Leu | Glu | Gly |
| | | | | 165 | | | | | 170 | | | | | 175 | |
| Ile | Gln | Leu | Ile | Ala | Lys | Lys | Ser | Lys | Asn | His | Ile | Gln | Trp | Leu | Gly |
| | | | 180 | | | | | 185 | | | | | 190 | | |
| Ser | His | Thr | Thr | Val | Gly | Val | Gly | Gly | Arg | Leu | Glu | Gly | Leu | Thr | Gln |
| | | | 195 | | | | | 200 | | | | | 205 | | |
| Asp | Leu | Arg | Gln | Leu | Gln | Glu | Ser | Glu | Gln | Gln | Leu | Asp | His | Leu | Met |
| | | 210 | | | | | 215 | | | | | 220 | | | |
| Asn | Ile | Cys | Thr | Thr | Gln | Leu | Arg | Leu | Leu | Ser | Glu | Asp | Thr | Asp | Ser |
| 225 | | | | | 230 | | | | | 235 | | | | | 240 |
| Gln | Arg | Leu | Ala | Tyr | Val | Thr | Cys | Gln | Asp | Leu | Arg | Ser | Ile | Ala | Asp |
| | | | | 245 | | | | | 250 | | | | | 255 | |
| Pro | Ala | Glu | Gln | Met | Val | Met | Val | Ile | Lys | Ala | Pro | Pro | Glu | Thr | Gln |
| | | | | 260 | | | | | 265 | | | | | 270 | |
| Leu | Gln | Ala | Val | Asp | Ser | Ser | Glu | Asn | Phe | Gln | Ile | Ser | Leu | Lys | Ser |
| | | | 275 | | | | | 280 | | | | | 285 | | |
| Lys | Gln | Gly | Pro | Ile | Asp | Val | Phe | Leu | Cys | Pro | Glu | Glu | Thr | Val | Gly |
| | | | 290 | | | | | 295 | | | | | 300 | | |
| Gly | Ile | Ser | Pro | Gly | Lys | Thr | Pro | Ser | Gln | Glu | Val | Thr | Ser | Glu | Glu |
| 305 | | | | | | 310 | | | | | 315 | | | | 320 |
| Glu | Asn | Arg | Ala | Thr | Asp | Ser | Ala | Thr | Ile | Val | Ser | Pro | Pro | Pro | Ser |
| | | | | 325 | | | | | 330 | | | | | 335 | |
| Ser | Pro | Pro | Ser | Ser | Leu | Thr | Thr | Asp | Pro | Ser | Gln | Ser | Leu | Leu | Ser |
| | | | | 340 | | | | | 345 | | | | | 350 | |
| Leu | Glu | Gln | Glu | Pro | Leu | Leu | Ser | Arg | Met | Gly | Ser | Leu | Arg | Ala | Pro |
| | | | 355 | | | | | 360 | | | | | 365 | | |
| Val | Asp | Glu | Asp | Arg | Leu | Ser | Pro | Leu | Val | Ala | Ala | Asp | Ser | Leu | Leu |
| | | | 370 | | | | | 375 | | | | | 380 | | |
| Glu | His | Val | Arg | Glu | Asp | Phe | Ser | Gly | Leu | Leu | Pro | Glu | Glu | Phe | Ile |

```
385                    390                    395                    400
Ser Leu Ser Pro Pro His Glu Ala Leu Asp Tyr His Phe Gly Leu Glu
                405                    410                    415

Glu Gly Glu Gly Ile Arg Asp Leu Phe Asp Cys Asp Phe Gly Asp Leu
                420                    425                    430

Thr Pro Leu Asp Phe
            435
```

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:14:

GCTCTAGAGC CCAGTATAGA         20

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:15:

GCTCTAGATG TCTCAAGCCT TTCCC         25

(2) INFORMATION FOR SEQ ID NO:16:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
Asp Glu Glu Asp Glu Glu Glu Asp Pro Ser Ser Pro Glu
 1               5                   10
```

(2) INFORMATION FOR SEQ ID NO:17:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
Val Ala Leu Ala Thr Gly Gln Leu Pro Ala Ser Asn Ser His Gln
 1               5                   10                  15
```

(2) INFORMATION FOR SEQ ID NO:18:

(i) SEQUENCE CHARACTERISTICS:
        (A) LENGTH: 17 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:18:

CACCCGCAAT GGTCACT                                                                                    17

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:19:

ATGTCTCAAG CCTTTCCC                                                                                   18

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:20:

GATAGAAAAC GAGCTAGAG                                                                                  19

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:21:

TTCTGAGAAA TCAGAGTCTA                                                                                 20